US010376489B2

(12) United States Patent
Martins-Green et al.

(10) Patent No.: US 10,376,489 B2
(45) Date of Patent: Aug. 13, 2019

(54) WOUND HEALING

(71) Applicant: The Regents of the University of California, Oakland, CA (US)

(72) Inventors: Manuela Martins-Green, Riverside, CA (US); Sandeep Dhall, Elkridge, MD (US); Danh Do, Baltimore, MD (US); Neal Schiller, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/492,649

(22) Filed: Apr. 20, 2017

(65) Prior Publication Data
US 2017/0252320 A1   Sep. 7, 2017

Related U.S. Application Data

(63) Continuation of application No. 15/162,570, filed on May 23, 2016, now abandoned.

(60) Provisional application No. 62/165,156, filed on May 21, 2015.

(51) Int. Cl.
*A61K 31/355* (2006.01)
*A61K 31/198* (2006.01)
*A61K 45/06* (2006.01)
*A61L 15/44* (2006.01)
*A61L 26/00* (2006.01)

(52) U.S. Cl.
CPC .......... *A61K 31/355* (2013.01); *A61K 31/198* (2013.01); *A61K 45/06* (2013.01); *A61L 15/44* (2013.01); *A61L 26/0066* (2013.01); *A61L 2300/412* (2013.01)

(58) Field of Classification Search
CPC . A61K 31/198; A61K 31/355; A61K 2300/00
See application file for complete search history.

(56) References Cited

PUBLICATIONS

Bajji et al. (Physiologia Plantarum 129: 472-483, 2007).*
Cho I. Blaser MJ: The human microbiome: at the interface of health and disease. Nat Rev Genet 2012, 13:260-70.
Grice E a, Snitkin ES, Yockey LJ, Bermudez DM, Liechty KW, Segre J a: Longitudinal shift in diabetic wound microbiota correlates with prolonged skin defense response. Proc Natl Acad Sci U S A 2010, 107:14799-804.
Khanna S., Biswas S, Shang Y, Collard E., Azad a, Kauh C. Shasker V. Gordillo GM, Sen CK. Roy S: Macrophage dysfunction impairs resolution of inflammation in the wounds of diabetic mice. PLoS One 2010, 5:e9539.
Daisuke K. Lee IK, Ishii H, Kanoh H, King GL: Prevention Treatment of Glomerular Dysfunction, with d-a-Tocopherol in Diabetic Rats by. J Am Soc Nephrol 1997, 8:426-435.
Diego-Otero Y de: α-Tocopherol Protects Against Oxidative Stress in the Fragile X Knockout Mouse an Experimental Therapeutic Approach for the Fmr1 Deficiency.pdf. 2009:1011-1026.
Ikeda S, Tohyama T, Yoshimura H, Hamamura K, Abe K, Yamashita K: Dietary alpha-tocopherol decreases alpha-tocotrienol but not gamma-tocotrienol concentration in rats. J Nutr 2003, 133:426-34.
Senoglu N, Yozbasiogla MF, Aral M, Ezberci M, Kurutas EB, Bulbuloglu E, Ezberci F. Oksuz H, Ciragil P: Protective effects of N-acetylcysteine and beta-glucan pretreatment on oxidative stress in cecal ligation and puncture model of sepsis. J Invest Surg 2008, 21:237-43.
Ivanovski O, Szumilak O, Nguyen-Khoa T, Ruellan N, Phan O, Lacour B, Descamps-Latscha B, Drüeke TB, Massy Z a: The antioxidant N-acetylcysteine prevents accelerated atherosclerosis in uremic apolipoprotein E knockout mice. Kidney Int 2005, 67:2288-94.
Han A, Zenilman JM, Melendez JH, Shirtliff ME, Agostinho A, James G, Stewart PS, Mongodin EF, Rao D, Rickard AH, Lazarus GS: The importance of a multifaceted approach to characterizing the microbial flora of chronic wounds. Wound Repair Regen 2011, 19:532-41.
James G, Marc A, Hunt A: Imaging Biofilms in Tissue Specimens. In Antibiofilm Agents. vol. 8. Edited by Rumbaugh KP, Ahmed I. Berlin, Heidelberg: Springer Berlin Heidelberg; 2014:31-44. [Springer Series on Biofilms].
Gilmore A.Shirley, Robinson Gretchen, Posthauer Ellen Mary RJ: Clinical Indicators Associated with Unintentional Weight loss and Pressure Ulcers in Elderly Residents of Nursing Facilities.pdf. 1995:984-992.
Scales BS, Huffnagle GB: The microbiome in wound repair and tissue fibrosis. J Pathol 2013, 229:323-31.
Grice EA, Segre JA: The skin microbiome. Nat Rev Microbiot 2011, 9:244-53.
Roth RR, James WD: Microbial ecology of the skin. Annu Rev Microbial 1988 42:441-64.
Hannah Trostrup, et al., "Animal models of chronic wound care: the application of biofilms in clinical research", Chronic Wound Care Management and Research 2016:3 pp. 123-132.
Brittany Winfield, "Topical Oxygen and Hyperbaric Oxygen Therapy Use and Healing Rates in Diabetic Foot Ulcers", Website: https://www.woundsresearch.com/article/topical-oxygen-and-hyperbaric-oxygen-therapy-use-and-healing-rates-diabetic-foot-ulcers; May 2014, Issue: vol. 26; Issue 5.
Maruyama K, Asai J, Ii M, Thorne T. Losordo DW, D'Amore P a: Decreased macrophage number and activation lead to reduce lymphatic vessel formation and contribute to impaired diabetic wound healing. Am J Pathol 2007, 170:1178-91.
Galiano RD, Tepper OM, Pelo CR, Bhatt K a, Callaghan M, Bastidas N, Bunting S, Steinmetz HG, Gurtner GC: Topical vascular endothelial growth factor accelerates diabetic wound healing through increased angiogenesis and by mobilizing and recruiting bone marrow-derived cells. Am J Pathol 2004, 164:1935-47.

(Continued)

*Primary Examiner* — Zohreh A Fay
(74) *Attorney, Agent, or Firm* — Brooks Kushman P.C.

(57) ABSTRACT

A method of treating a chronic wound in a subject in need of such treatment is provided. The method includes administering to the subject at least one antioxidant agent in an amount effective to treat the wound. In some versions, the antioxidant agent is α-tocopherol or N-acetyl cysteine, or a combination of these compounds. In other versions, a method of preparing a chronic wound animal model is provided.

12 Claims, 19 Drawing Sheets

(56) References Cited

PUBLICATIONS

Lobmann R, Ambrosch a, Schultz G, Waldmann K, Schiweck S. Lehnert H: Expression of matrix-metalloproteinases and their inhibitors in the wounds of diabetic and non-diabetic patients. Diabetologia 2002, 45:1011-6.

Sen CK, Gordillo GM, Roy S. Kirsner R. Lambert L, Hunt TK, Gottrup F, Gurtner GC, Longaker MT: Human skin wounds: a major and snowballing threat to public health and the economy. Wound Repair Regen 2009, 17:763-71.

National Diabetes Statistics Report: Estimates of Diabetes and Its Burden in the United States [http //www.cdc.gov/diabetes/pubs/statsreport14.htm].

Wlaschek M, Scharffetter-Kochanek K: Oxidative stress in chronic venous leg ulcers. Wound Repair Regen 2005, 13:452-61.

James G a, Swogger E, Wolcott R. Pulcini E deLancey, Secor P, Sestrich J, Costerton JW. Stewart PS: Biofilms in chronic woulds. Wound Repair Regen 2007, 16:37-44.

Bjarnsholt T. Kirketerp-Møller K, Jensen PØ, Madsen KG, Phipps R, Krogfelt K, Høiby N. Givskov M: Why chronic wounds will not heal: a novel hypothesis. Wound Repair Regen 2008, 16:2-10.

Greenhalgh DG, Sprugel KH, Murray MJ, Ross R: PDGF and FGF stimulate wound healing in the genetically diabetic mouse. Am J Pathol 1990, 136:1235-46.

Kishimoto TK, Jutila MA, Berg EL, Butcher EC: Neutrophil Mac-1 and MEL-14 adhesion proteins inversely regulated by chemotactic factors. Science 1989, 245:1238-41.

Ponugoti B, Xu F, Zhang C, Tian C, Pacios S, Graves DT: FOXO1 promotes wound healing though the up-regulation of TGF-β1 and prevention of oxidative stress. J Cell Biol 2013, 203:327-43.

Sen CK, Roy S: Redox signals in wound healing. Biochim Biophys Acta 2008, 1780:1348-61.

Gjødsbøl K, Christensen JJ, Karlsmark T. Jørgensen B, Klein BM, Krogfelt KA: Multiple bacterial species reside in chronic wounds: a longitudinal study. Int Wound J 2006, 3:225-31.

Christensen GD, Simpson W a, Younger JJ, Baddour LM, Barrett FF, Melton DM, Beachey EH: Adherence of coagulase-negative Staphylococci to plastic tissue culture plates: a quantitative model for the adherence of Staphylococci to medical devices. J Clin Microbiol 1985, 22:998-1006.

Kolodkin-Gal I. Cao S, Chai L. Böttcher T. Kolter R, Clardy J, Losick R: A self-produced trigger for biofilm disassembly that targets exopolysaccharide. Cell 2012, 149 684-92.

Dhall S, Do D. Garcia M, Wijesinghe DS, Brandon A, Kim J, Sanchez A, Lyubovitsky J, Gallagher S, Nothnagel EA, Chalfant CE, Patel RP, Schiller N, Martins-Green M: A novel model of chronic wounds: importance of redox imbalance and biofilm-forming bacteria for establishment of chronicity: PLoS One 2014, 9:e109848.

Gilbert A: New Colorimetric Methods of Sugar Analysis. Methods Enzymol 1962, 184:85-95.

Chaplin MF: A rapid and sensitive method for the analysis of carbohydrate components in glycoproteins using gas-liquid chromatography. Anal Biochem 1982, 123:336-341.

Chambers RE, Clamp JR: An assessment of methanolysis and other factors used in the analysis of carbohydrate-containing materials. Biochem J 1971, 125:1009-18.

Fu H, Yadav MP, Nothnagel EA: Physcomitrella patens arabinogalactan proteins contain abundant terminal 3-O-methyl-L: -rhamnosyl residues not found in angiosperms. Planta 2007, 226:1511-24.

Mustoe T a, O'Shaughnessy K, Kloeters O: Chronic wound pathogenesis and current treatment strategies: a unifying hypothesis. Plast Reconstr Surg 2006. 117(7 Suppl):35S-41S.

Bonomo SR, Davidson JD, Tyrone JW, Lin X, Mustoe T a: Enhancement of wound heating by hyperbaric oxygen and transforming growth factor beta3 in a new chronic wound model in aged rabbits. Arch Surg 2000, 135:1148-53.

Feinstein RN. Berliner S. Green F: Mechanism of Inhibition of Catalase by 3-Amino-1,2,4-triazole. Arch Biochem Biophys 1957, 76:32-44.

Heim WG, Appleman D, Pyfrom HT: Effects of 3-Amino-I. 2,4-Triazole (AT) on Catalase and Other Compounds. Am J Physiol 1956, 186:19-23.

Legg PG, Wood RL: Effects of catalase inhititors on the ultrastructure and peroxidase activity of proliferating microbodies. Histochemie 1970, 22:262-76.

Neurobiology B: Pergamon Effects of 3-Amino-I , 2 , 4-Triazole on Brain Catalase in the Mediation of Ethanol Consumption in Mice. 1994, 11:235-239.

Guidet BR, Shah S V: In vivo generation of hydrogen peroxide by rat kidney cortex and glomeruli. Am J Physiol 1989, 256(1 Pt 2):F158-64.

Welker AF, Campos ÉG, Cardoso LA, Hermes-Iima M: Role of catalase on the hypoxia / reoxygenation stress in the hypoxia-tolerant Nile tilapia. 2012.

Amantea D, Marrone MC, Nisticò R, Frederici M, Bagetta G, Bernardi G. Mercuri NB: Oxidative stress in stroke pathophysiology validation of hydrogen peroxide metabolism as a pharmacological target to afford neuroprotection. In Int Rev Neurobiol. vol. 85: 2009:363-74.

Himes D: Protein-calorie malnutrition and involuntary weight loss: the role of aggressive nutritional intervention in wound healing. Ostomy Would Manage 1999, 45:46-51, 54-5.

Siddiqui AR, Bernstein JM: Chronic wound infection facts and controversies. Clin Dermatol 2010, 28:519-26.

Percival SL. Hill KE, Malic S, Thomas DW, Williams DW: Antimicrobial tolerance and the significance of persister cells in recalcitrant chronic wound biofilms. Wound Repair Regen 2010, 19:1-9.

Sebeny PJ, Riddle MS, Petersen K: Acinetobacter baumannii skin and soft-tissue infection associated with war trauma. Clin Infect Dis 2008, 47:444-9.

Dowd SE, Sun Y, Secor PR. Rhoads DD, Wolcott BM, James G a, Wolcott RD: Survey of bacterial diversity in chronic wounds using pyrosequencing, DGGE, and full ribosome shotgun sequencing. BMC Microbiol 2008, 8:43.

Be N a, Allen JE, Brown TS, Gardner SN. McLoughlin KS, Forsberg J a, Kirkup BC, Chromy B a, Luciw P a, Ester E a, Jaing CJ: Microbial profiling of combat wound infection through detection microarray and next-generation sequencing. J Clin Microbiol (May 2014).

Ma C, Martins-Green M: Second-hand cigarette smoke inhibits wound healing of the cornea by stimulating inflammation that delays corneal reepithelialization. Wound Repair Regen 2009, 17:387-96.

D'Autréaux B, Toledano MB: ROS as signalling molecules: mechanisms that generate specificity in ROS homeostasis. Nat Rev Mol Cell Biol 2007, 8:813-24.

Loo AEK, Wang YT. Ho R, Wasser M, Du T, Ng WT, Halliwell B: Effects of hydrogen peroxide on wound healing in mice in relation to oxidative damage. PLoS One 2012, 7:e49215.

Dröge W: Free radicals in the physiological control of cell function. Physiol Rev 2002, 82:47-95.

James TJ. Hughes M a, Cherry GW, Taylor RP: Evidence of oxidative stress in chronic venous ulcers. Wound Repair Regen 2003, 11:172-6.

Petreaca ML, Do D, Dhall S, McLelland D, Serafino A, Lyubovitsky J, Schiller N, Martins-Green MM: Deletion of a tumor necrosis superfamily gene in mice leads to impaired healing that mimics chronic wounds in humans. Wound Repair Regen 2012, 20:353-66.

Mudge BP, Harris C. Gilmont RR, Adamson BS, Rees RS: Role of glutathione redox dysfunction in diabetic wounds. Wound Repair Regen 2002, 10:52-8.

Chaudiere J, Wilhelmsen EC, Tappel a L: Mechanism of selenium-glutathione peroxidase and its inhibition by mercaptocarboxylic acids and other mercaptans. J Biol Chem 1984, 259:1043-50.

Kingma JG, Simard D, Rouleau JR, Tanguay RM, Currie RW: Effect of 3-aminotriazole on hyperthermia-mediated cardioprotection in rabbits. Am J Physiol 1996, 270(4 Pt 2):H1165-71.

(56) References Cited

PUBLICATIONS

Roy S, Khanna S, Nallu K, Hunt TK, Sen CK: Dermal wound healing is subject to redox control. Mol Ther 2006. 13:211-20.
Schafer M, Werner S: Oxidative stress in normal and impaired wound repair. Pharmacol Res 2008, 58:165-71.

* cited by examiner

| CMIC of GPx/CAT inhibitor treated wounds | |
|---|---|
| | Amoxicillin (µg/mL) |
| Day 4 | 6-13 |
| Day 18 | 13-25 |
| Day 26 | 50-100 |
| Day 56 | >200 |

CMIC= Community minimal inhibitory concentration

FIG. 9

Gm = Gentamicin
Cb = Carbenicillin
Amox = Amoxicillin

| CMIC of NAC/αToc Treated Wounds | | | |
|---|---|---|---|
| | Amox (µg/mL) | Cb (µg/mL) | Gm (µg/mL) |
| Day 20 | 25 | 25-50 | 13-25 |
| Day 30 | 13-25 | 13 | 3-6 |
| Day 40 | 6-13 | 6-13 | 3-6 |
| Day 50 | 6-13 | 6-13 | 3-6 |

FIG. 17

Day 30 Dbdb + IAE

Day 30 Dbdb + IAE
+ 10 days AOA

Day 40 Dbdb + IAE

Day 40 Dbdb + IAE
+ 20 days AOA

WOUND HEALING

CROSS-REFERENCE TO RELATED APPLICATIONS

This application is a continuation of application Ser. No. 15/162,570, filed on May 23, 2016, which claims the benefit of Provisional Patent Application No. 62/165,156, filed on May 21, 2015, all of which are incorporated by reference herein.

STATEMENT REGARDING FEDERALLY SPONSORED RESEARCH OR DEVELOPMENT

This invention was made in part with Government support under Grant No. R21A1078208 from the National Institutes of Health, National Institute of Allergy and Infectious Diseases. The Government has certain rights in this invention.

BACKGROUND

Field of the Invention

The invention relates to creating and treating wounds.

Related Art

Wound healing is a dynamic process involving many factors and cell types including soluble mediators, blood cells, fibroblasts, endothelial cells, and extracellular matrix. Normal wound healing is divided into several sequential phases that overlap in space and time: homeostasis, inflammation, granulation tissue formation, and tissue remodeling. Chronic wounds develop as a result of defective regulation of one or more of the complex molecular and biological events involved in proper healing.

Chronic wounds in diabetics are one of the most common complications. Diabetic foot ulcers and other similar chronic wounds impact ~6.5M people and cost ~$25 B/year in the US alone. The critical need for a cure of diabetic chronic wounds is underlined by the continuous increase in type II diabetes which accounts for 90-95% of all diabetes. Challenges in doing research and understanding these problematic wounds result from varying disease etiologies, existing co-morbidities and, importantly difficulties with human tissue collection. For the most part, a clinician sees the patient when the wound is already at an advanced stage of chronicity and critical evidence of causality is already lost.

Oxidative and nitrosative stress that make up the redox environment have been at the epicenter of numerous diseases. Maintaining balance of the redox state in the body is a challenge and hence a variety of methods and drugs have been used to meet this need for balance.

SUMMARY

In one aspect, a method of treating a wound in a subject in need of such treatment is provided. The method includes administering to the subject at least one antioxidant agent in an amount effective to treat the wound. In some embodiments: a) the at least one antioxidant agent decreases wound infection; b) the at least one antioxidant agent increases the rate of wound healing; c) the at least one antioxidant agent is two or more antioxidant agents; d) the at least one antioxidant agent comprises a free radical scavenger, a lipid peroxidation inhibitor, or a combination thereof; e) the at least one antioxidant agent comprises N-acetyl cysteine, vitamin A, vitamin C, vitamin E, α-tocopherol, glutathione, lipoic acid, carotenes, coenzyme Q (ubiquinol), melatonin, ellagic acid, punicic acid, luteolin, catalase, superoxide dismutase, peroxiredoxins, cysteine, flavenoids, phenolics, or ergothioneine, or a physiological salt thereof, or any combination thereof; f) the at least one antioxidant agent comprises α-tocopherol (α-TOC), N-acetyl cysteine, a physiological salt thereof, or any combination thereof; g) the wound is a chronic wound; h) the wound is a frankly chronic wound; i) the wound contains exudate; j) the treating comprises dismantling of the biofilm, improvement in the re-epithelialization of the wound, improvement in maturity of the granulation tissue of the wound, decrease in wound infection, resolution of inflammation, increase in rate of wound healing, establishment of homeostasis, or any combination thereof; k) the subject is a human or animal; l) the subject is a diabetic; m) the wound is treated by debridement before administering at least one antioxidant agent; n) or any combination of a)-m).

In some embodiments, the wound is a chronic wound. In these embodiments, the wound may or may not contain exudate. In some embodiments, the wound is a frankly chronic wound.

In another aspect, a method of making a chronic wound mouse model is provided. The method includes creating a fresh wound in a db/db mouse, administering to the mouse one or more inhibitors of at least one antioxidant agent, and allowing the fresh wound to develop into a chronic wound. In some embodiments, a) the administering is performed before creating the fresh wound, after creating the fresh wound, or before and after creating the fresh wound; b) the inhibitors can be 3-amino-1,2,4-triazole, mercaptosuccinic acid, or a combination thereof; c) the method further comprises covering the fresh wound with a dressing, which can be a film-type dressing; d) the routes of administration for the one or more inhibitors can be intradermal, transdermal, parenteral, intravenous, intramuscular, intranasal, subcutaneous, percutaneous, intratracheal, intraperitoneal, topical, systemic, perfusion, lavage, direct injection, oral administration and formulation, or any combination thereof; e) the antioxidant agent is involved in wound healing; f) or any combination of a)-e).

In further aspects, a chronic wound mouse model and a method of using the mouse model to screen for agents that can treat and/or promote healing of chronic wounds are provided.

BRIEF DESCRIPTION OF THE DRAWINGS

For a more complete understanding of the present invention, reference is now made to the following descriptions taken in conjunction with the accompanying drawings, in which:

In FIG. 7A, Growth potential, the dashed line represents the levels of growth above which the bacterial have the capacity to form biofilm.

FIG. 7B shows the same bacteria growth on specific media to identify the various species.

FIG. 9 is a table of antibiotic resistance as the biofilm develops over time.

FIG. 17 is a table indicating that antibiotic resistance decreased as the wounds are treated with AOA over time. This is the case for 3 antibiotics used in the clinic.

DETAILED DESCRIPTION

Figure 1:
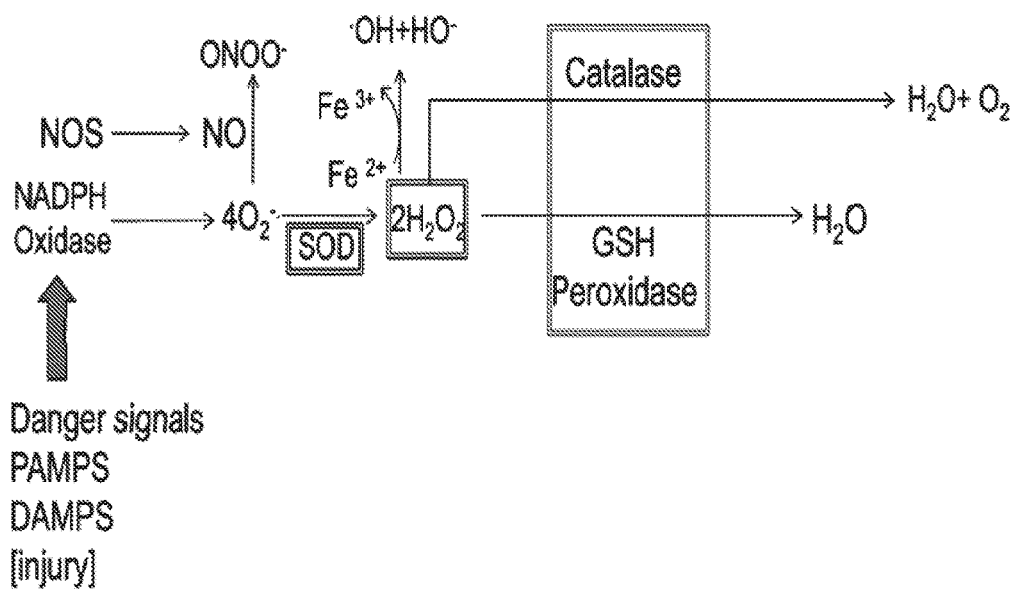
FIG. 1 is a simplified schematic illustration of the oxidative and nitrosative stress cycle.

In one aspect, a method of treating a wound in a subject is provided. The method includes administering to the subject at least one antioxidant agent in an amount effective to treat the wound. In some embodiments, the wound can be a chronic wound. Chronic wounds include, but are not limited to, venous stasis ulcers, arterial ulcers, diabetic ulcers, pressure ulcers, traumatic ulcers, post-surgical ulcers, small vascular wounds, wounds with bacterial biofilm, and allergy-induced wounds. Chronic wounds occur in diseases and conditions such as, but not limited to, diabetes, vasculitis, ischemia, immune suppression, pyoderma gangrenosum, fibrosis, edema, sickle cell anemia, and peripheral arterial disease atherosclerosis.

In some embodiments, the at least one antioxidant agent is one antioxidant agent, two antioxidant agents, or more than two antioxidant agents. An antioxidant agent can be, but is not limited to, a free radical scavenger or an inhibitor of lipid peroxidation, or a combination thereof.

Examples of antioxidant agents include, but are not limited to, N-acetyl cysteine, vitamin A, vitamin C, vitamin E, glutathione, lipoic acid, carotenes, coenzyme Q (ubiquinol), melatonin, ellagic acid, punicic acid, luteolin, catalase, superoxide dismutase, peroxiredoxins, cysteine, flavenoids, phenolics, and ergothioneine, or a physiological salt thereof, or a combination thereof. Any form of vitamin E can be used, including tocopherols such as α-tocopherol, and tocotrienols.

An antioxidant agent can be administered to a subject in various ways depending, for example, on the particular antioxidant agent and the type of wound. The routes of administration can include, e.g., intradermal, transdermal, parenteral, intravenous, intramuscular, intranasal, subcutaneous, percutaneous, intratracheal, intraperitoneal, topical, systemic, perfusion, lavage, direct injection, and oral administration and formulation. In embodiments having multiple antioxidant agents, the different agents can be administered by the same or different routes.

The length of administration will vary depending on, for example, the antioxidant agent or agents used, the subject being treated, the subject's weight, the manner of administration and the judgment of the prescribing physician. For example, administration of the active agent or compound can occur for at least 20 days once a wound is chronic, or until the wound is visibly improved and on the way to healing.

In embodiments of the method, an antioxidant agent can be administered in an amount effective to treat the wound, or when two or more antioxidant are administered, each agent alone or a combination of the agents is in an amount effective to treat the wound. This therapeutically effective amount is an amount that results in an improvement or a desired change in the condition for which the agent or combination is administered, whether the agent or combination is administered once or over a period of time. For example, with respect to methods of treating a wound, the improvement can be a dismantling of the biofilm, improvement in the re-epithelialization of the wound, improvement in maturity of the granulation tissue of the wound, decrease in wound infection, resolution of inflammation, increase in rate of wound healing, establishment of homeostasis, or any combination thereof. As is known, the therapeutically effective amount will vary depending on, for example, the antioxidant agent or agents employed, the subject being treated, the subject's weight, the manner of administration and the judgment of the prescribing physician. With a diabetic subject, the levels of agent in the blood and the health condition of the subject can also be a consideration. In a mouse subject, for example, 200 mg/kg body weight of N-acetyl cysteine (equivalent to a 10% solution) and 50 mg/kg body weight of α-tocopherol (equivalent to a 20% solution) can be administered. Similar doses, appropriately scaled, can be used for humans.

In some embodiments, the antioxidant agent can be administered as a pharmaceutical composition. A pharmaceutical composition will typically contain a pharmaceutically acceptable carrier. Depending on the intended mode of administration, the pharmaceutical compositions may be in the form of solid, semi-solid or liquid dosage forms, such as, for example, tablets, suppositories, pills, capsules, powders, liquids, suspensions, ointments or lotions, preferably in unit dosage form suitable for single administration of a precise dosage. The compositions may include an effective amount of a selected compound in combination with a pharmaceutically acceptable carrier and, in addition, may include other pharmaceutical agents such as anti-viral agents, adjuvants, diluents, buffers, and the like. The compound may thus be administered in dosage formulations containing conventional non-toxic pharmaceutically acceptable carriers, adjuvants and vehicles.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions may, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine acetate, triethanolamine oleate, etc. Actual methods of preparing such dosage forms are known, or will be apparent, to those skilled in this art. For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like. One skilled in this art may further formulate the compound in an appropriate manner, and in accordance with accepted practices, such as those disclosed in Remington's Pharmaceutical Sciences, Gennaro, Ed., Mack Publishing Co., Easton, Pa. 1990.

A salt of an antioxidant agent can be a physiologically acceptable salt, which can be a pharmaceutically acceptable salt. Physiologically acceptable salts and pharmaceutically acceptable salts are well known in the art and include salts prepared from pharmaceutically acceptable non-toxic acids, including inorganic acids and organic acids. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic acids, and the like. Salts formed with, for example, a free carboxy group of an amino acid residue or a peptide, can be derived from inorganic bases including, but not limited to, sodium, potassium, ammonium, calcium or ferric hydroxides, and organic bases including, but not limited to, isopropylamine, trimethylamine, histidine, and procaine.

The subject can be a human or another animal, such as another mammal.

The present invention may be better understood by referring to the accompanying examples, which are intended for illustration purposes only and should not in any sense be construed as limiting the scope of the invention.

Example 1

The methods in this Example were described in Sandeep Dhall, Danh C. Do, Monika Garcia, et al., "Generating and Reversing Chronic Wounds in Diabetic Mice by Manipulating Wound Redox Parameters," Journal of Diabetes Research, vol. 2014, Article ID 562625, 18 pages, 2014. doi: 10.1155/2014/562625, incorporated by reference herein.

Dermal Excision Wound Model, Preparation of Tissue for Extracts and for Histology The surgical procedures discussed here were approved by the Institutional Animal Care and Use Committee of the University of California, Riverside. Buprenex and ATZ are administered 30 and 20 minutes before surgery, respectively. The mouse is then placed in an enclosed container that is hooked up to a isoflurane vaporizer in the chemical hood. Once the mouse is knocked out or no longer moving, it is placed on a white surgical pad and the head is fitted with a nose cone that is secured to allow continuous administration of isoflurane for the duration of the surgery. A wipe (Kimwipe) sprayed with 70% ethanol or a clinical ethanol towelette is used to lightly wipe the area where the wound will be made (to minimize killing of the normal bacterial present in the skin). This also provides a clean surface for the tegaderm to stick well since dust from the bedding, food, or skin can prevent the tegaderm from sticking properly. Full thickness 7 mm punch wounds (excision of the skin and the underlying panniculus carnosus) were made on the back of the mice. The animals were euthanized using carbon-dioxide at various time points and the wound tissue was collected for histology and protein analysis using a 10 mm punch (wound bed+surrounding tissue). For protein analysis, zirconium oxide beads weighing approximately the same as the wound tissue were added to tissue in safe lock tubes, followed by addition of 10 μL of RIPA buffer per mg of tissue. The tissues were bullet blended for homogenization. The extracts were then centrifuged at 14000 rpm for 15 minutes at 4° C. The supernatants were used fresh or aliquots prepared and stored at −80° C. for later use. The samples were normalized to protein levels.

Superoxide Dismutase Activity Assay

Total tissue superoxide dismutase (SOD) activity was measured by using a commercially available kit (Cayman Chemical, Catalog number 706002, Ann Arbor, USA) that measures all three types of SOD (Cu/Zn-, Mn-, and EC-SOD). One unit of SOD is defined as the amount of enzyme needed to cause 50% dismutation of the superoxide radical. Briefly, xanthine oxidase and hypoxanthine generate superoxide radicals that are dismutated by SOD and in the process tetrazolium salt are converted to a formazan dye that is read at 450 nm. The SOD activity of the samples was calculated from the linear regression of a standard curve that was determined using the SOD activity of bovine erythrocytes at various concentrations run under the same conditions. The SOD activity was expressed as U/mL of tissue extract.

Hydrogen Peroxide Activity Assay

Tissue hydrogen peroxide ($H_2O_2$) levels were measured by using a commercially available kit (Cell Technology Inc., Catalog number FLOH 100-3, Mountain View, USA) that utilizes a nonfluorescent detection reagent. The assay is based on the peroxidase-catalyzed oxidation by $H_2O_2$ of the nonfluorescent substrate 10-acetyl-3,7-dihydroxyphenoxazine to a fluorescent resorufin. 50 μL of tissue extracts collected at different time points after wounding and normalized to protein concentration was mixed with 50 μL of the reaction cocktail in an opaque 96-well assay plate. Fluorescent intensities were measured at 530 nm (excitation)/590 nm (emission) using a Victor 2 (fluorescence and absorbance) microplate reader. The amounts of $H_2O_2$ in the supernatants were derived from a seven-point standard curve generated with known concentrations of $H_2O_2$.

Catalase Activity Assay

Tissue catalase activity was measured by using a commercially available kit (Cayman Chemical, Catalog number 707002, Ann Arbor, USA). The enzyme assay for catalase is based on the peroxidatic function of catalase with methanol to produce formaldehyde in the presence of an optimal concentration of $H_2O_2$. The formaldehyde produced was measured spectrophotometrically, with 4-amino-3-hydrazino-5-mercapto-1,2,4-triazole (purpald) as the chromogen, at 540 nm in a 96-well place. The catalase activity was expressed as nmol/min/mL of tissue extract.

Glutathione Peroxidase Activity Assay

A commercially available kit (Cayman Chemical, Catalog number 703102, Ann Arbor, USA) was used to measure tissue glutathione peroxidase (GPx) activity. The activity was measured indirectly by a coupled reaction with glutathione reductase (GR). GPx reduces $H_2O_2$ to $H_2O$ and in the process oxidized glutathione (GSSG) is produced that in turn is recycled to its reduced state by GR and NADPH. Oxidation of NADPH to NADP+ is accompanied by a decrease in absorbance at 340 nm. Under conditions in which GPx activity is rate limiting, the rate of decrease in the absorbance measured at 340 nm, in a 96-well plate at 1 min interval for a total of 5 min using a Victor 2 microplate reader, is directly proportional to the GPx activity of the sample. GPx activity was expressed as nmol/min/mL of tissue extract.

Chronic Wound Model

To generate chronic wounds in db/db mice we performed full thickness 7 mm diameter excision wounds on the dorsum of 6-7-month-old mice. Twenty minutes prior to wounding, mice were treated once intraperitoneally (IP) with 3-amino-1,2,4-triazole (ATZ) (Aldrich Chemistry; St. Louis, Mo.) at 1 g/kg body weight, an inhibitor for catalase. Immediately after wounding, they were treated once topically with the inhibitor for GPx, mercaptosuccinic acid (MSA), (Sigma Lifesciences; St. Louis, Mo.) at 150 mg/kg body weight. Immediately after wounding, the wounds were covered with tegaderm (3 M; St. Paul, Minn.) to prevent contamination and were kept covered for the duration of the experiments. In these mice it is easy to fully remove the hair from the back and hair grows very slowly; hence we had no problems keeping the tegaderm in place. The tegaderm was removed periodically to take pictures of the wound and then immediately replaced. The wounds were fully chronic 20 days after wounding and remained open sometimes for more than 3 months, depending on the experiment. Control db/db mice were treated exactly the same way but instead of inhibitors of the antioxidant enzymes they were treated with the vehicle (PBS). To reverse chronicity, at 20 days, the antioxidant NAC (Aldrich Chemistry (St. Louis, Mo.)) was topically applied to the wound at 200 mg/kg and the tegaderm replaced. Simultaneously, the mice were injected intraperitoneally with α-toc, Sigma Lifesciences (St. Louis, Mo.) at 50 mg/kg. This treatment continued with NAC applied to the wound topically every day using an insulin syringe to deposit the solution under the tegaderm and over the wound and with α-toc IP every other day for 20 days (40 days after wounding). At this point, the antioxidant treatment was stopped and the wounds went on to heal around 30 days after initiation of treatment with antioxidants (50 days after wounding). For the antioxidant controls, the mice were treated exactly the same but with vehicle rather than antioxidants. In some experiments, tissues were collected at various time points for detailed histological/histochemical, biochemical, and cellular/molecular evaluation, and in some cases the tissues were analyzed for type and level of bacterial infection/biofilm production. Chronic wounds were successfully created in over 100 animals Bacteria Isolation and Characterization To obtain the wound microbiome samples we used sterile cotton Q-tips to swab the wound bed, including the surface of the wound, but yet minimizing disruption of the wound microenvironment to allow for longitudinal studies of the microbiome. The content of each swab was suspended in 1.0% w/v protease peptone and 20.0% v/v glycerol solution. Wounded tissue for bacteria analysis was obtained using sterile scissors and suspended in 1.0% w/v protease peptone and 20.0% v/v glycerol solution. Tissues were homogenized in the presence of zirconium oxide beads using a bullet blender at 4° C. Bacteria were cultured for 16-18 h at 37° C. on tryptic soy agar plates (BD Difco, Sparks, Md.), containing 5.0% v/v defibrinated sheep blood (Colorado Serum Company, Denver, Colo.), and 0.08% w/v Congo red dye (Aldrich Chemistry, St. Louis, Mo.). Colonies were differentiated and isolated based on size, hemolytic pattern, and Congo red uptake. Resulting cultures were examined using Gram stain and visualized with optical microscopy. Gram-negative rods were characterized using the API20E identification kit (Biomerieux, Durham, N.C.) and oxidase test (Fluka Analytical, St. Louis, Mo.). When required, the Pseudomonas Isolation Agar culture test, 42° C. growth test in tryptic soy broth (TSB) (BD Difco, Sparks, Md.), and motility test were used. Gram positive cocci cultures were differentiated based on catalase activity and coagulation activity (Fluka Analytical, St. Louis, Mo.), 6.5% w/v NaCl tolerance test, and hemolytic activity. Biofilm production was quantified using methods described previously with minor modifications. Briefly, 3-5 μL of the wound swabbed sample was seeded in 100 μL of TSB and grown in humidified incubator at 37° C. in a 96-well polystyrene flat bottomed tissue culture plate under static condition. Bacterial content was removed by inverting and gently flicking the plate. The plate was washed three times by slowly submerging the plate and gently flicking the inverted plate to remove the water. The wells were dried by tapping onto absorbent paper and then air dried at 65° C. for 30 minutes. The plate was cooled and stained with Hucker crystal violet for 5 minutes. Excessive stain was removed by rinsing the plate with water and then air dried overnight. The optical density at 570 nm was then taken using the SpectraMax M2e microplate reader (Molecular Device, Sunnyvale, Calif.). Samples that give an OD of or above 0.125 were considered biofilm positive whereas OD below 0.125 was considered biofilm negative.

Viable Bacteria Cells Count

Wound swab samples were resuspended in sterile Luria broth (LB) to yield a 1:4 v/v ratio of sample-to-TSB solution. Bacterial colonies were visually counted on trypticase soy agar plates containing 5% sheep red blood cells incubated at 37° C. overnight in a humidified incubator.

Community Minimal Inhibitory Concentrations Assay

Wound swab samples (containing bacteria) that were seeded on flat bottomed tissue culture plates for 3-4 hr at 37° C. in a humidified incubator were challenged with antibiotic for 12 hr at various concentrations in TSB. Optical density at 595 nm (OD 595 nm) was used to quantify bacterial growth. The community minimal inhibitory concentration (CMIC) is defined as the lowest concentration of antibiotic that resulted in <50% increase in OD 595 nm compared to that before introduction of antibiotic.

Bacterial Staining

Frozen sections of chronic wound tissues were stained using ViaGram Red+Bacterial Gram-Stain and Viability Kit (Life Technologies, Carlsbad, Calif.) with modifications to the manufacturer's protocol. Briefly, the frozen tissue sections were washed in 1×PBS for 5 minutes at room temperature to remove the OCT. Sections were then incubated in wheat germ agglutinin (WGA) conjugate stock solution for 5 minutes. The WGA solution was drained off the slide followed by the addition of 2.5 μL of the DAPI/Sytox Green working solution for 10 minutes at room temperature. The excess working solution was then removed from the section. Sections were mounted and visualized using a Nikon Microphot-FXA microscope with a Nikon DS-Fi1 digital camera.

Scanning Electron Microscopy

Tissues collected were fixed in 4% paraformaldehyde for 4 hrs at room temperature and then processed as described previously. Briefly, samples were dehydrated in a series of ethanol for 20 min each followed by critical point drying of the tissues, using Balzers CPD0202 and Au/Pd sputtering in the Sputter coater Cressington 108 auto. The samples were imaged using an XL30 FEG scanning electron microscope.

Biofilm Carbohydrate Composition

Chronic wound swab samples were washed with 80% and 100% ethanol to eliminate low molecular weight components and then with 2:1 (v/v) chloroform:methanol to remove lipids and acetone in preparation for drying. Samples were desiccated under vacuum in the presence of $P_2O_5$. Total protein content of the dried swab sample was estimated by the Lowry protein assay. Total carbohydrate content of dried swab sample was estimated by colorimetric phenol-sulfuric acid assay, using gum arabic as the standard. For glycosyl composition analysis, dried swab sample was cleaved by trifluoroacetic acid hydrolysis and the resulting monosaccharides were derivatized by methanolysis, N-acetylation, and trimethylsilylation as described previously, with minor modifications. Gas chromatography-flame ionization detection and gas chromatography-mass spectrometry were performed as previously described. DNA was extracted using the DNeasy Blood and Tissue kit (Qiagen, Chatsworth, Calif.) according to the manufacturer's instructions. DNA concentration was measured and purity confirmed by calculating the OD 260/OD 280 absorption ratio.

Second Harmonic Generation (SHG) Imaging

SHG imaging was done as previously described. Equipped with an NLO interface for a femtosecond Titanium-Sapphire laser excitation source (Chameleon-Ultra, Coherent, Incorporated, Santa Clara, Calif.) for multiphoton excitation, an inverted Zeiss LSM 510 NLO META laser scanning microscope (Carl Zeiss Microscopy, LLC, Thornwood, N.Y.) for transmitted light and epifluorescence was used. The Chameleon laser provided femtosecond pulses at a repetition rate of about 80 MHz, with the center frequency tunable from 690 to 1040 nm. A long working distance objective (Zeiss, 40× water, N.A. 0.8) was used to acquire images. The sample two-photon signals were epicollected and discriminated by the short pass 650 nm dichroic beam splitter. A META detection module with signals sampled in a 394-405 nm detection range (lex=800 nm) was used to collect the SHG images. Each image presented in this work is 12 bit, 512×512 pixels representing 225 mm×225 mm field of view.

Statistical Analysis

We used Graphpad Instat Software and Sigmaplot Software. Analysis of variance (ANOVA) was used to test significance of group differences between two or more groups. In experiments with only two groups, we used the Student's-test. Because the differences we observe are not small, we perform experiments in groups of three mice and then repeat the experiment in groups of three as many times as needed to be confident of the results. For the majority of the cases, 2 sets of experiments to a total of 6 animals were sufficient to achieve significant results.

Example 2

This Example shows whether early reduction in the antioxidant capacity immediately after wounding leads to the development of chronic wounds and whether application of antioxidants to these chronic ulcers reduces the oxidative stress and leads to restoration of normal healing.

Figure 2:
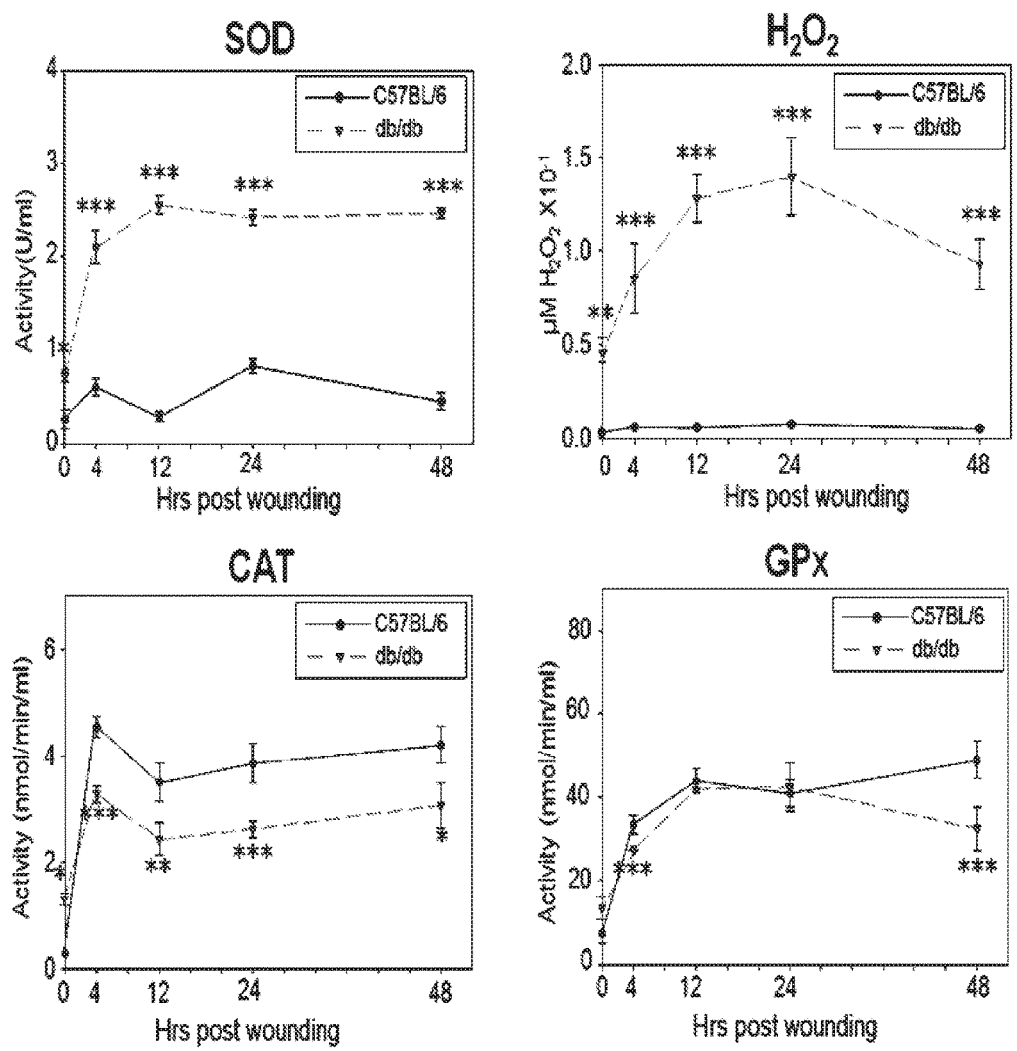
FIG. 2 is a panel of graphs showing the levels of superoxide dismutase (SOD), $H_2O_2$, catalase (CAT) and glutathione peroxidase (GPx) after wounding.
Figure 3:
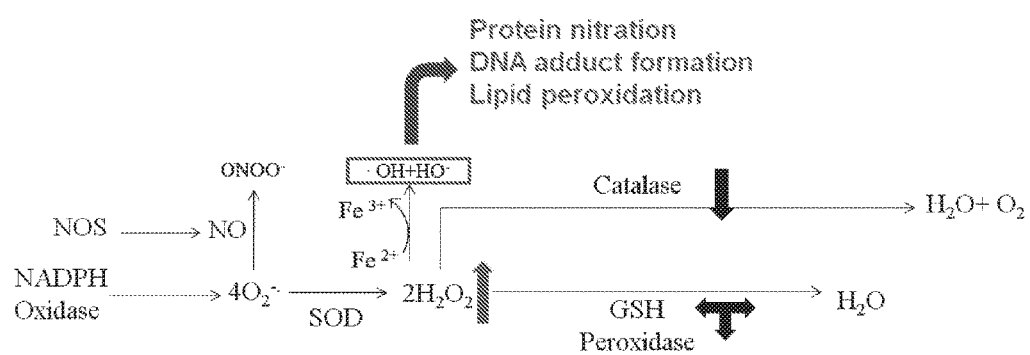
FIG. 3 is a schematic drawing of the oxidative and nitrosative stress cycle showing the effects of OH radicals.

I. Excessive Redox Environment in Impaired Wounds of the Diabetic Mouse Model, db/db$^{-/-}$, Mimics the Environment Present in Human Chronic Wounds Understanding how wounds become chronic will provide insights to reverse chronicity. We hypothesized that the high levels of oxidative stress (OS) in wound tissue is a critical component for generation of chronicity. To test this possibility we used the db/db$^{-/-}$ model of impaired healing and tested for key molecules involved in oxidative stress during wound healing (data are shown in the Figures). FIG. 1 shows a simplified version of the ROS/NOS cycle. We examined the levels of the molecules depicted in the boxes (FIG. 2). As early as 4 hrs after wounding, we showed that SOD (superoxide dismutase) is elevated as it tries to dismutate the superoxide anions ($O_2.^-$) to $H_2O_2$ which is also highly elevated (FIG. 2), and much like in humans, those levels increase with age. In addition, we also show that the two most potent antioxidant enzymes present in the wound, catalase and glutathione peroxidase (GPx), which process $H_2O_2$ to $H_2O$ and $O_2$, are down regulated or not changed, respectively, resulting in the building of $H_2O_2$ in the wound tissue (FIG. 2). The increased $H_2O_2$ can react with $Fe^{2+}$ ions to produce .OH radicals which are a highly damaging molecule to proteins, lipids and DNA (FIG. 3). Together these data show high levels of Reactive Oxidative Species (ROS) in the wound.

Figure 4:
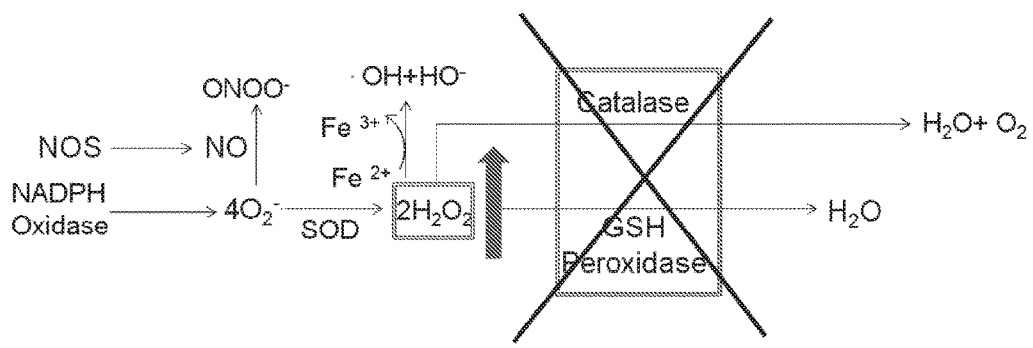
FIG. 4 is a schematic drawing of a gain of ROS function experiment.
Figure 5:
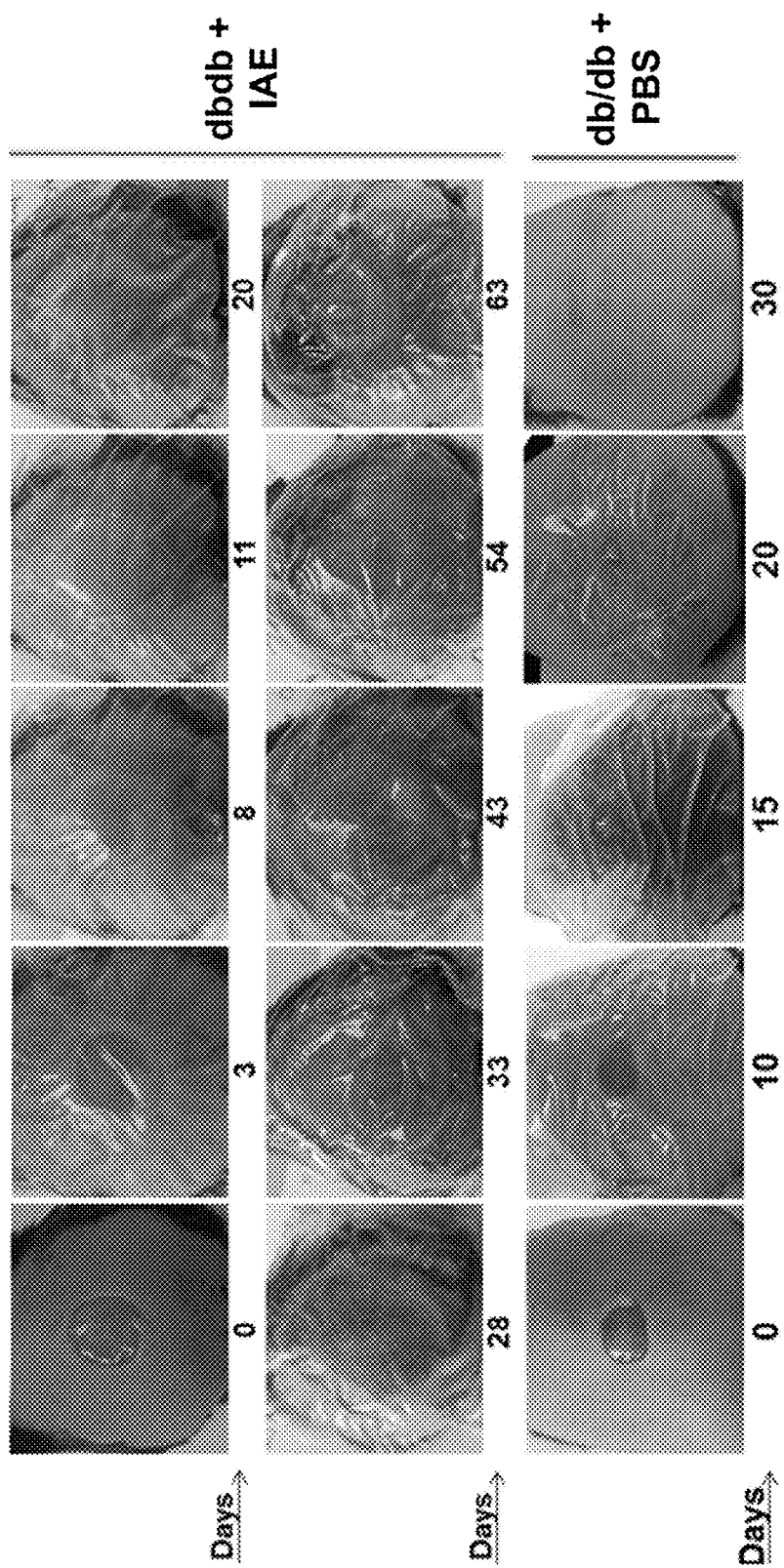
FIG. 5 is a panel showing results of inhibiting anti-oxidant enzymes.
Figure 6:
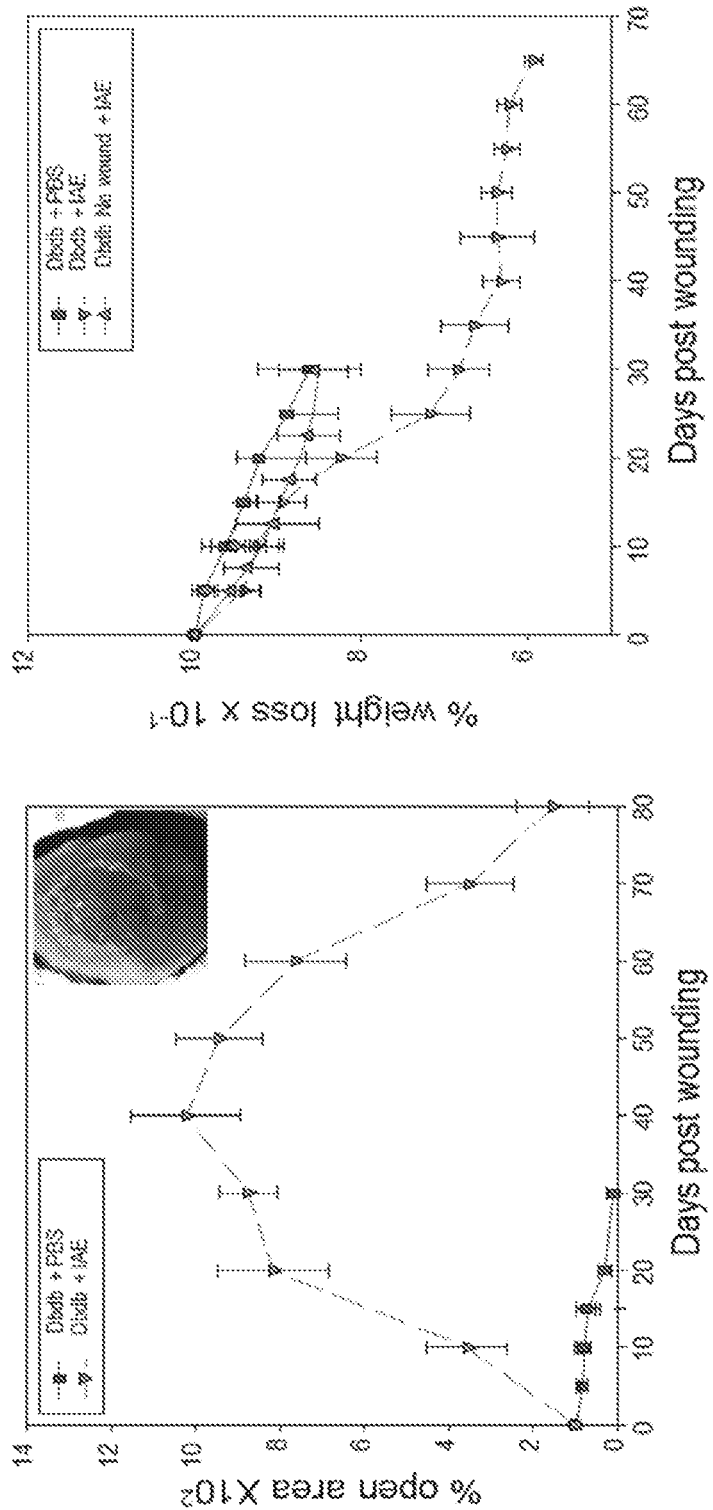
FIG. 6 is a panel showing wound areas on the left graph and animal weight on the right graph.
Figure 7B:
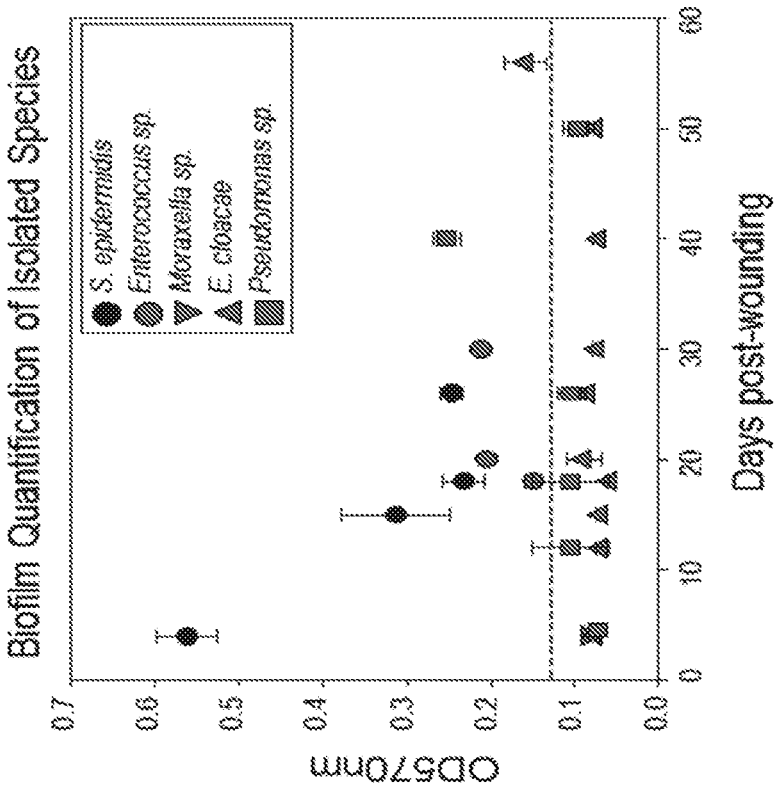
FIGS. 7A and 7B are graphs characterizing bacterial quantification and biofilm formation.
Figure 7A:
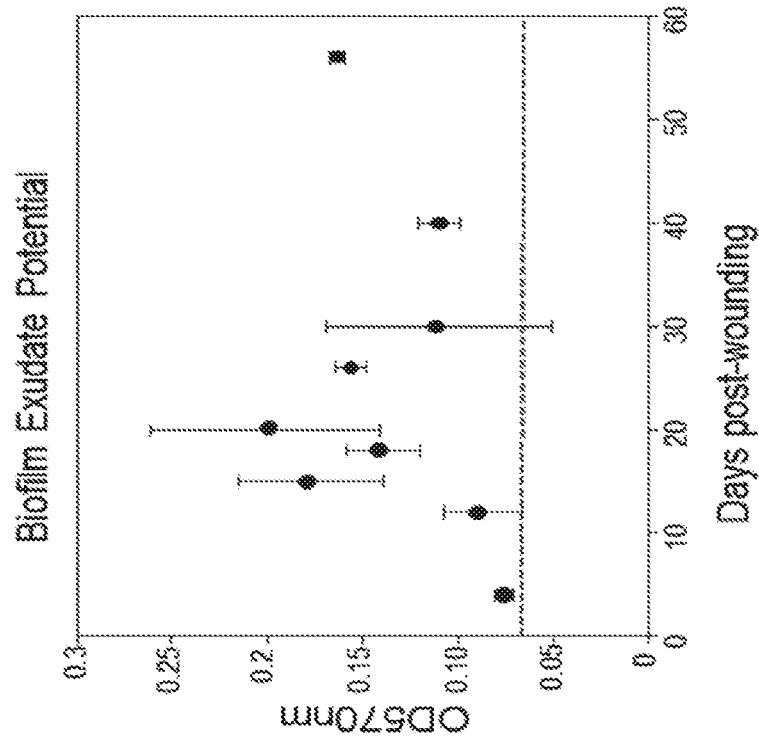
Figure 8:
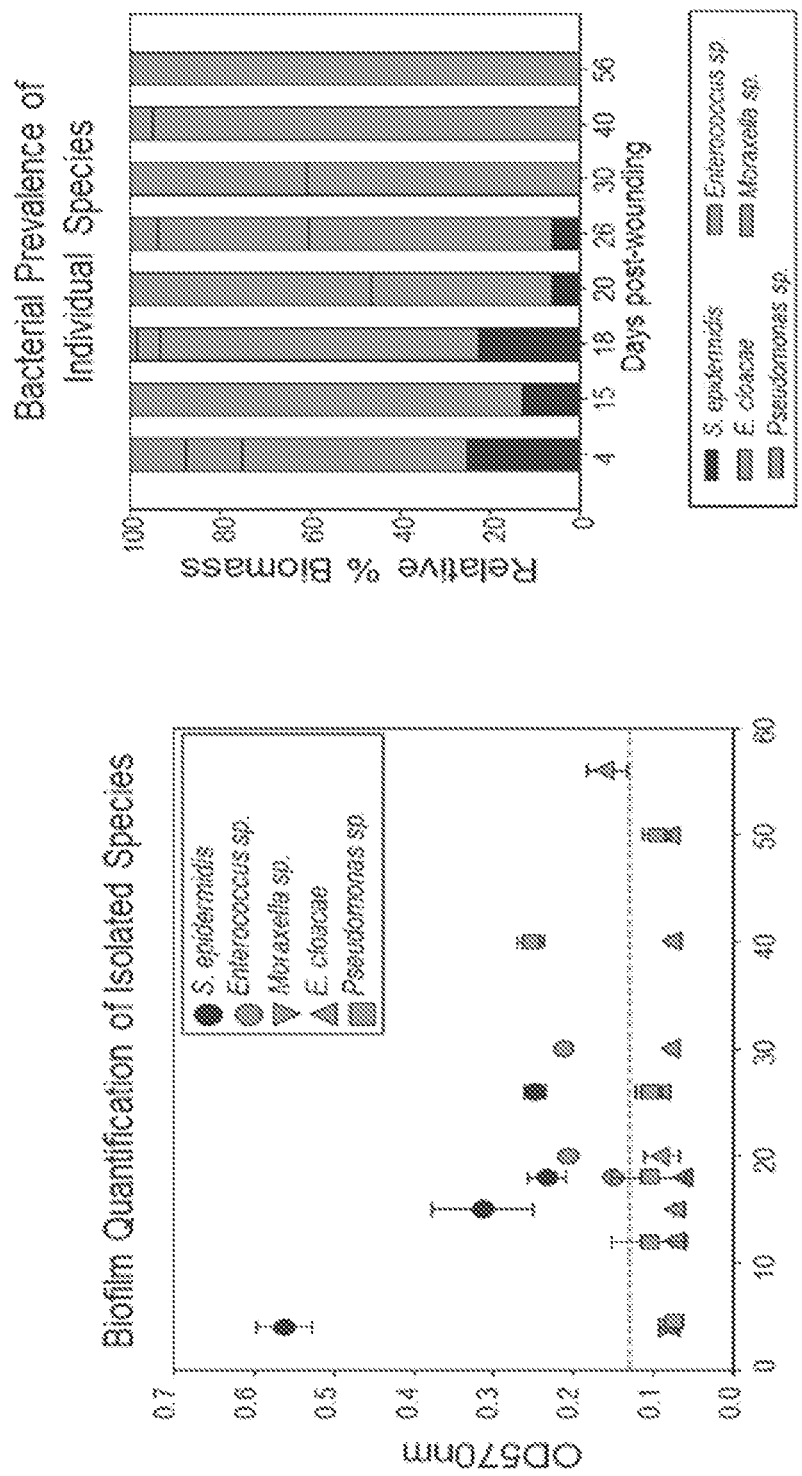
FIG. 8 is a panel of graphs characterizing bacterial quantification and biofilm formation. The left graph shows bacteria growth on specific media to identify various species as in FIG. 7B. The right graph shows the data of the left graph in a different configuration to more clearly show the bacteria competition during evolution of the biofilm formation.
Figure 10:
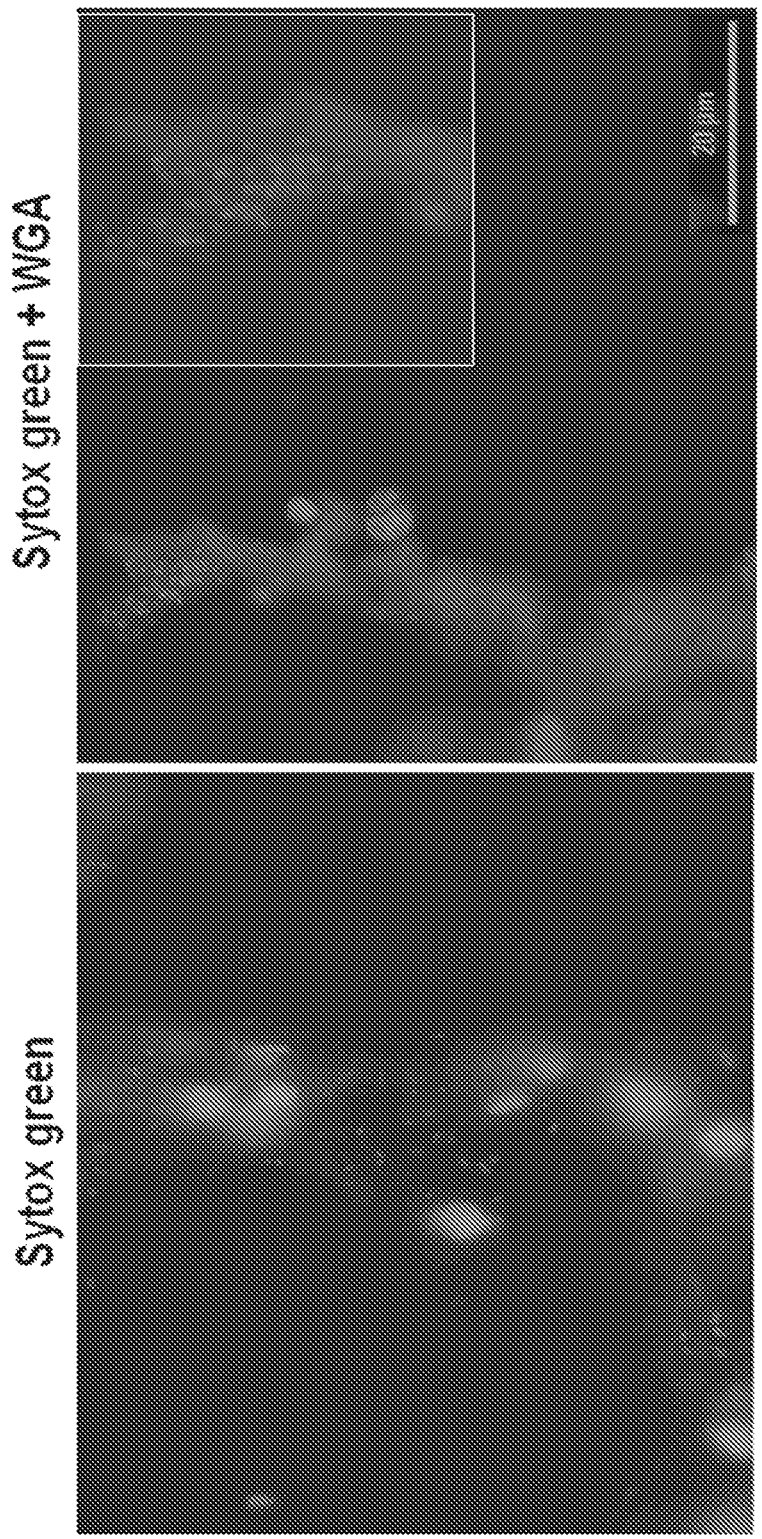
FIG. 10 is a panel indicating the presence of bacteria in the tissues of chronic wounds. In the left picture, small specks of green show the bacterial nuclei and large blobs show the cellular DNA. In the right picture, simultaneous staining with wheat germ agglutinin (WGA) shows close association of the bacteria with the biofilm.
Figure 11:
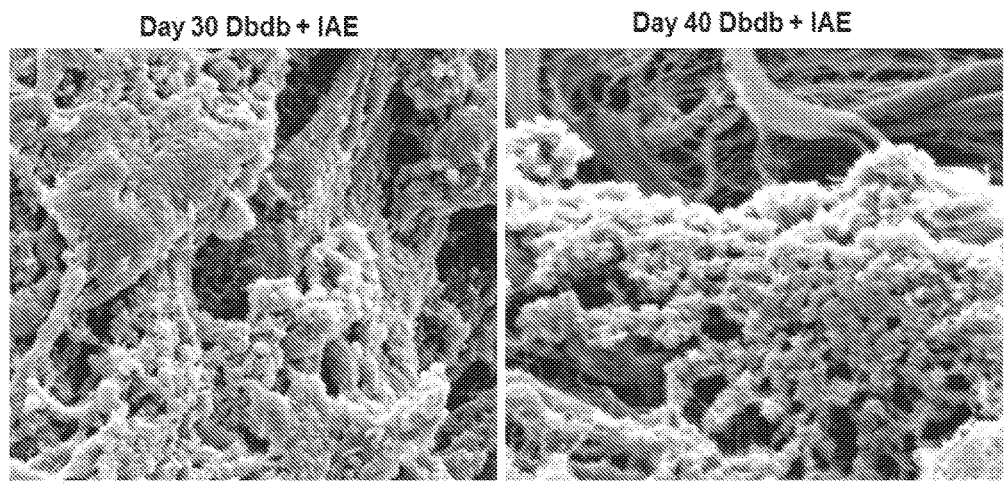
FIG. 11 is a panel of scanning electron micrographs indicating the presence of bacteria in the tissues of chronic wounds. Both micrographs show the biofilm is extensive on the surface of the wound.

II. Manipulation of Specific Redox Parameters in the Wound Environment Can Create and Reverse Chronic Wounds To show that these ROS are critical for the development of chronic wounds we perform gain and loss of function experiments. For the gain of function experiments, we further increased ROS in the wound tissue by inhibiting the Catalase and GPx, the two powerful anti-oxidant enzymes mentioned above, using specific inhibitors for their activity. At the time of wounding, catalase was inhibited with 3-Amino-1,2,4-triazole (ATZ) and GPx with mercaptosuccinic acid (MSA) (FIG. 4). Right after treatment the wound were covered with tegaderm a dressing approve for human use. In the figures these are called IAE (inhibitor of antioxidant enzymes). For details of the methodology see Dhall et al., 2014 (Dhall et al., Journal of Diabetes Research, Volume 2014, Article ID 562625) and Example 1 above. This treatment applied at the time of wounding was necessary and sufficient to cause the wounds to become chronic producing exudate and biofilm whereas treatment with PBS, used as a vehicle for the delivery of the enzyme inhibitors, heal in the normal time period for these mice (FIG. 5). The wound area enlarges and the mice lose weight (FIG. 6). The biofilm develops with time without any manipulation on our part and is composed of many different bacteria that have been found in human chronic wounds (FIGS. 7A, 7B, and 8). With time the various biofilm forming bacteria compete with each other and in the end one, E. cloacae, wins. Presence of biofilm was confirmed by antibiotic treatment, and microscopy. The former showed clearly that at day 4 when there is no biofilm forming capacity (FIGS. 7A and 7B) the antibiotic dose needed to eliminate the bacteria is low but that increases dramatically over time as the biofilm forms (FIG. 9). For the microscopic observations we use sytox green to visualize the bacteria I the tissue and wheat germ agglutinin to see the biofilm matrix (FIG. 10). We also used scanning electron microscopy to visualize the biofilm on the surface of the wound (FIG. 11).

Figure 12:
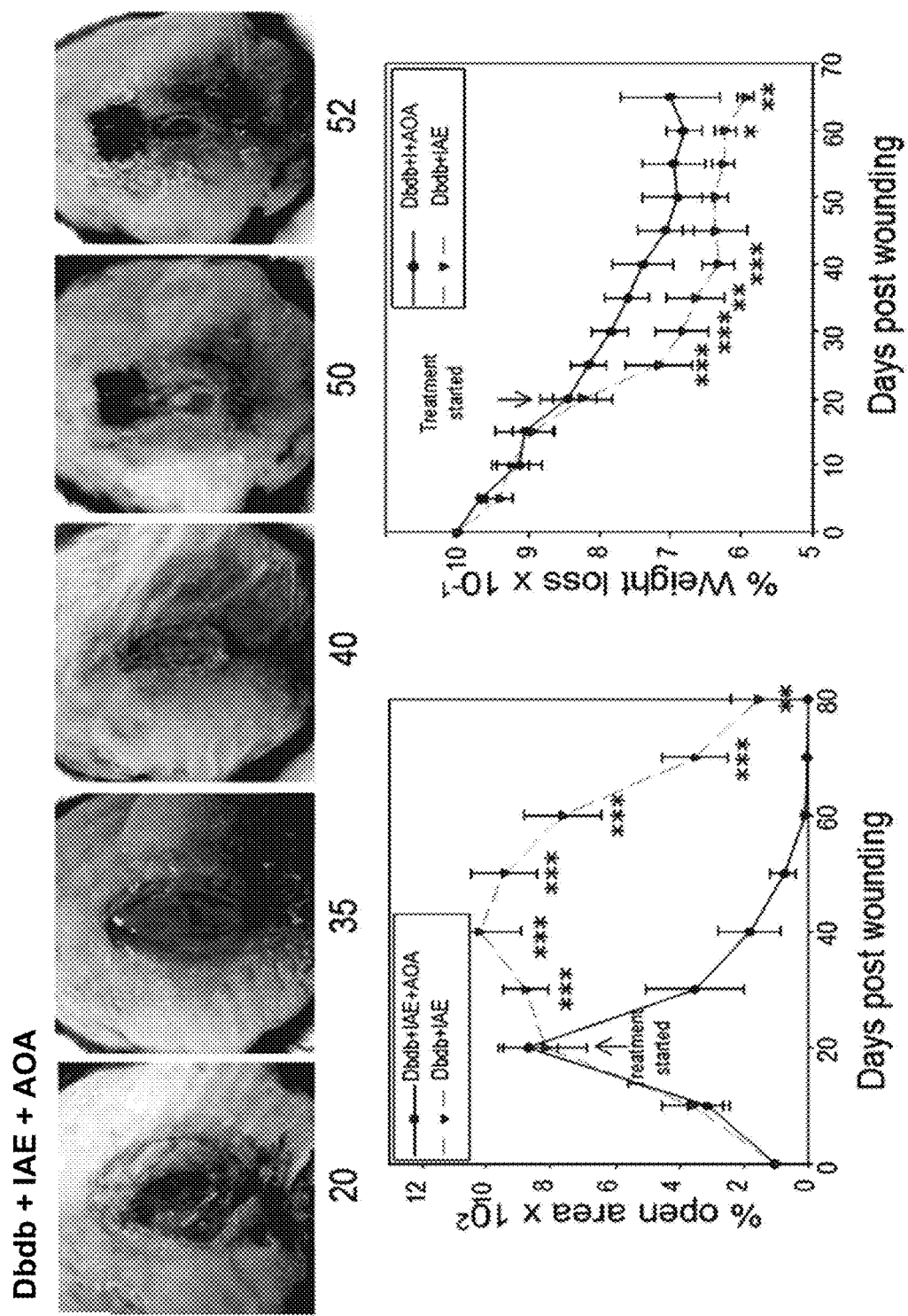
FIG. 12 is a panel indicating that treatment with N-acetyl cysteine and α-tocopherol improves healing and weight gain. The photos illustrate the improvement in healing after Antioxidant Agent (AOA) treatment. The graph on the left shows great improvement in size of the wound area and the graph on the right shows weight recovery after AOA treatment.
Figure 13:
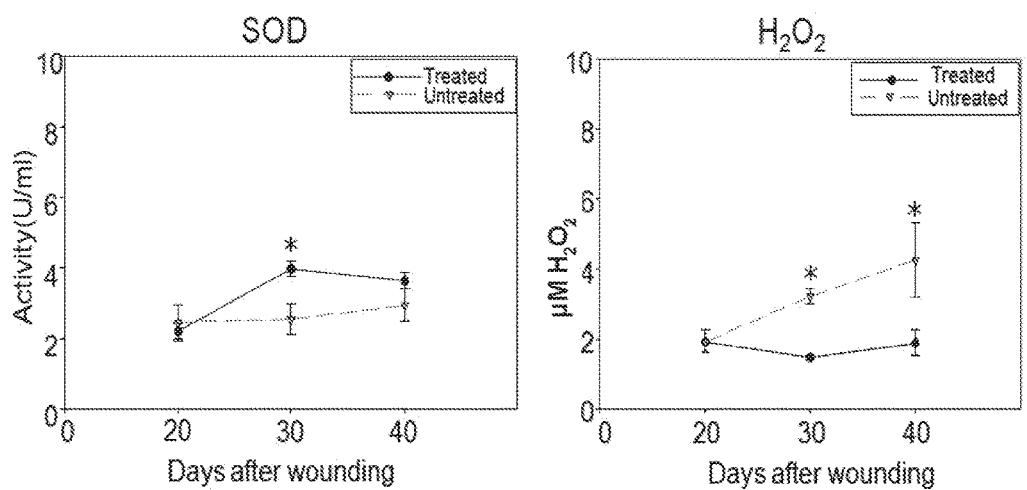
FIG. 13 is a panel indicating that treatment with N-acetyl cysteine and α-tocopherol decreases oxidative stress. The graph on the left shows that superoxide dismutase (SOD) is elevated as it tries to dismutate superoxide anions into $H_2O_2$. The graph on the right shows that $H_2O_2$ is lower because the antioxidant enzyme activity is now elevated compared with the non-treated wounds (see FIG. 14).
Figure 14:
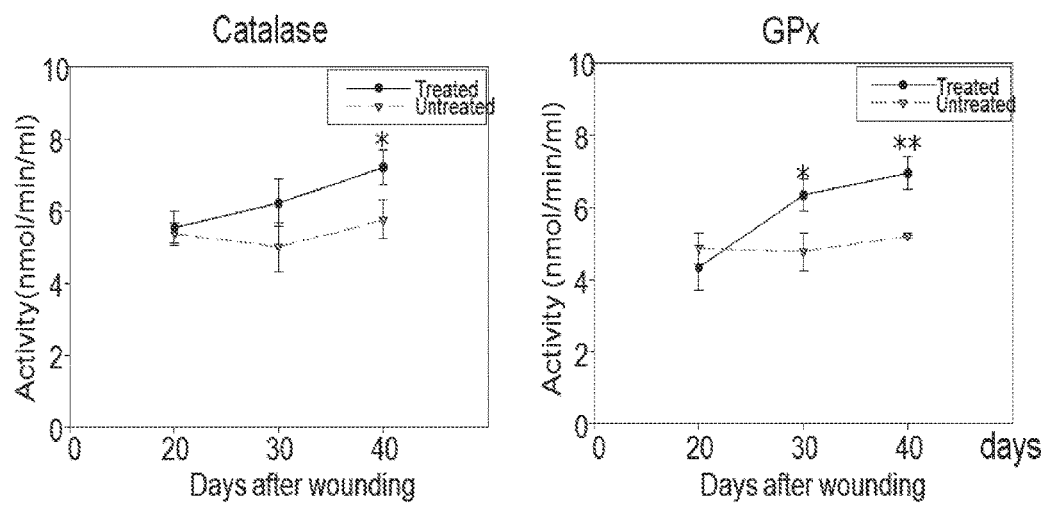
FIG. 14 is a panel indicating that treatment with N-acetyl cysteine and α-tocopherol decreases oxidative stress. Both anti-oxidant enzymes catalase (left graph) and glutathione peroxidase (GPx; right graph) are elevated in the wounds treated with the antioxidant agents (AOA).
Figure 15:
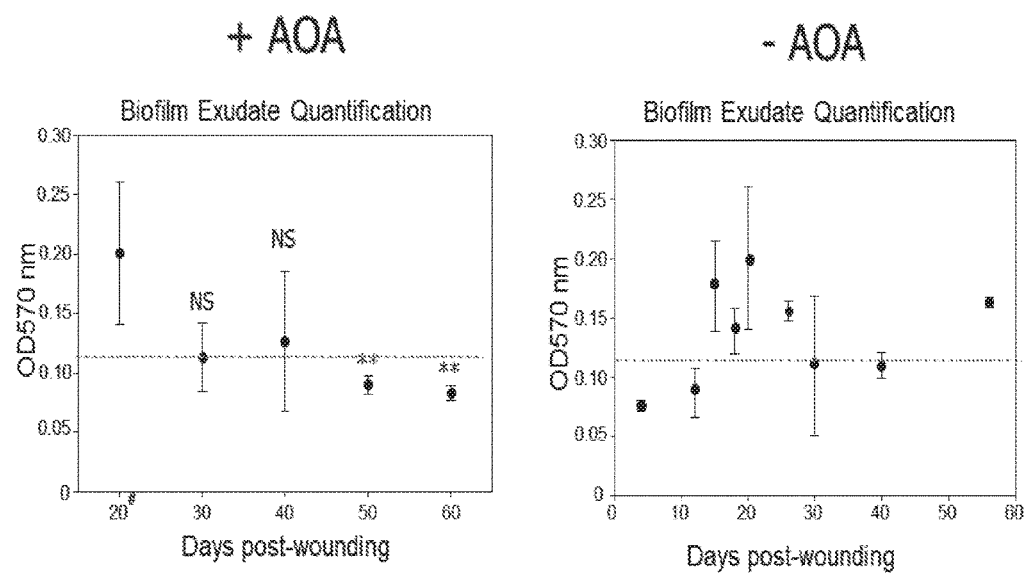
FIG. 15 is a panel indicating that treatment with N-acetyl cysteine and α-tocopherol decreases bacterial burden. The potential for biofilm formation is significantly decreased when the chronic wounds are treated with AOA (left graph) when compared to non-treated (right graph).
Figure 16:
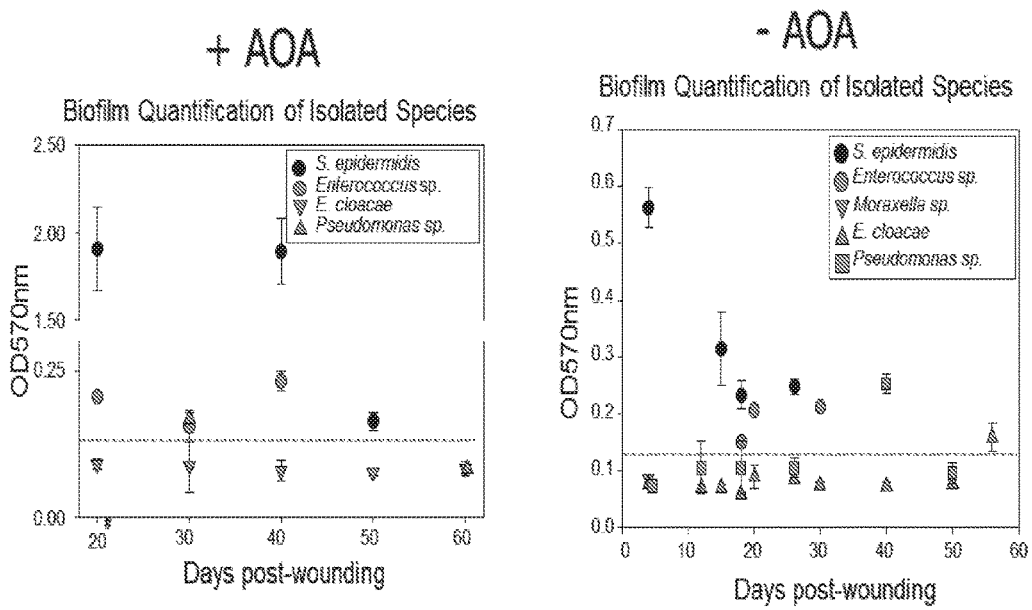
FIG. 16 is a panel indicating that treatment with N-acetyl cysteine and α-tocopherol decreases bacterial burden. Biofilm formation by the isolated species is significantly decreased when the chronic wounds are treated with AOA (left graph) when compared to non-treated (right graph).
Figure 18:
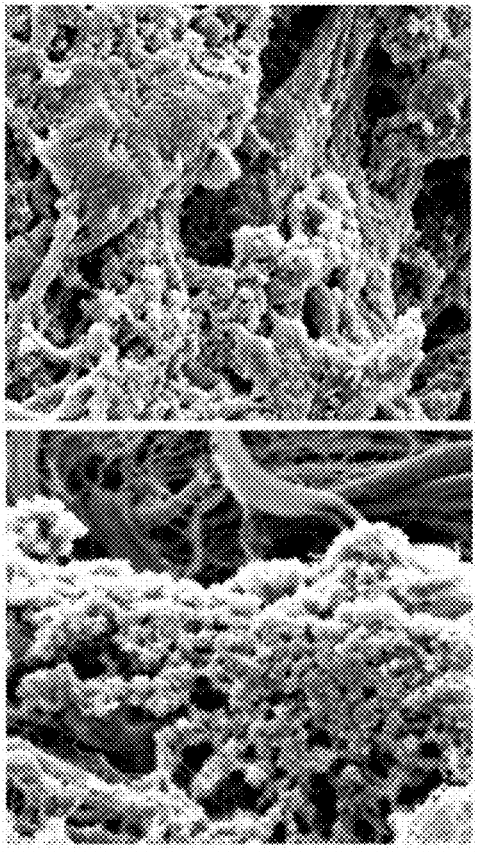
FIG. 18 is a panel of scanning electron micrographs showing that the biofilm is disappearing as the treatment continues (micrographs on the right compare with micrographs on the left).
Figure 18:
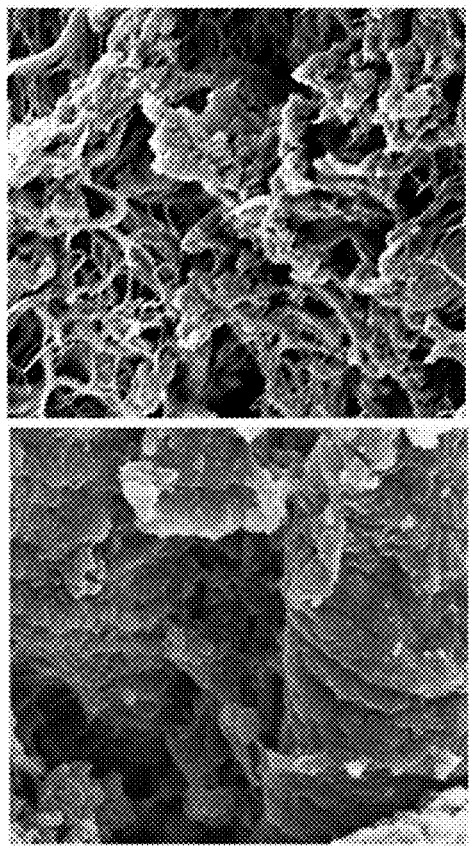
Figure 19:
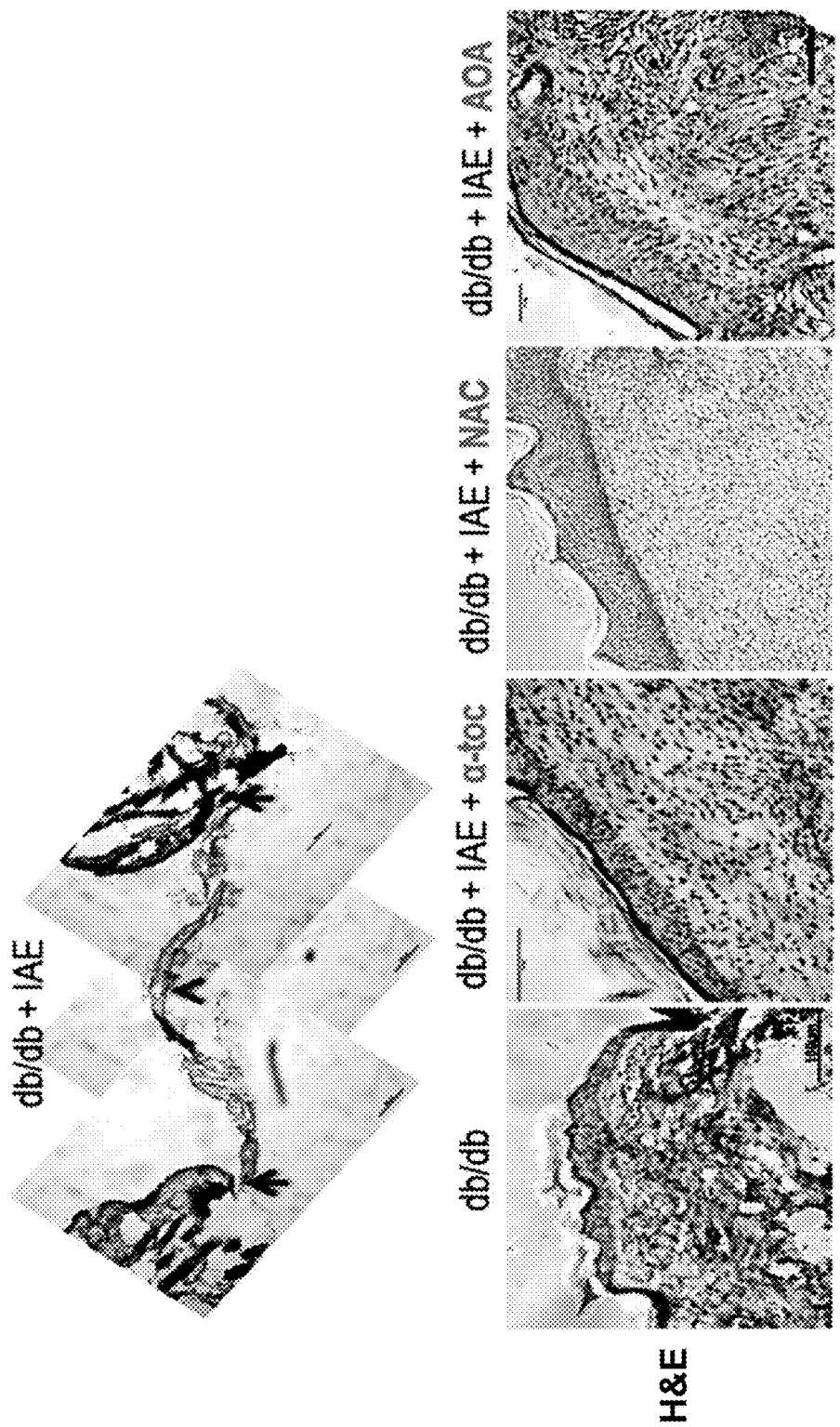
FIG. 19 is a panel indicating that treatment with N-acetyl cysteine and α-tocopherol improves the quality of the healing tissue. The pictures indicate that the granulation tissue is much more mature in the wounds treated with both AOA (NAC and a-Toc).
Figure 20:
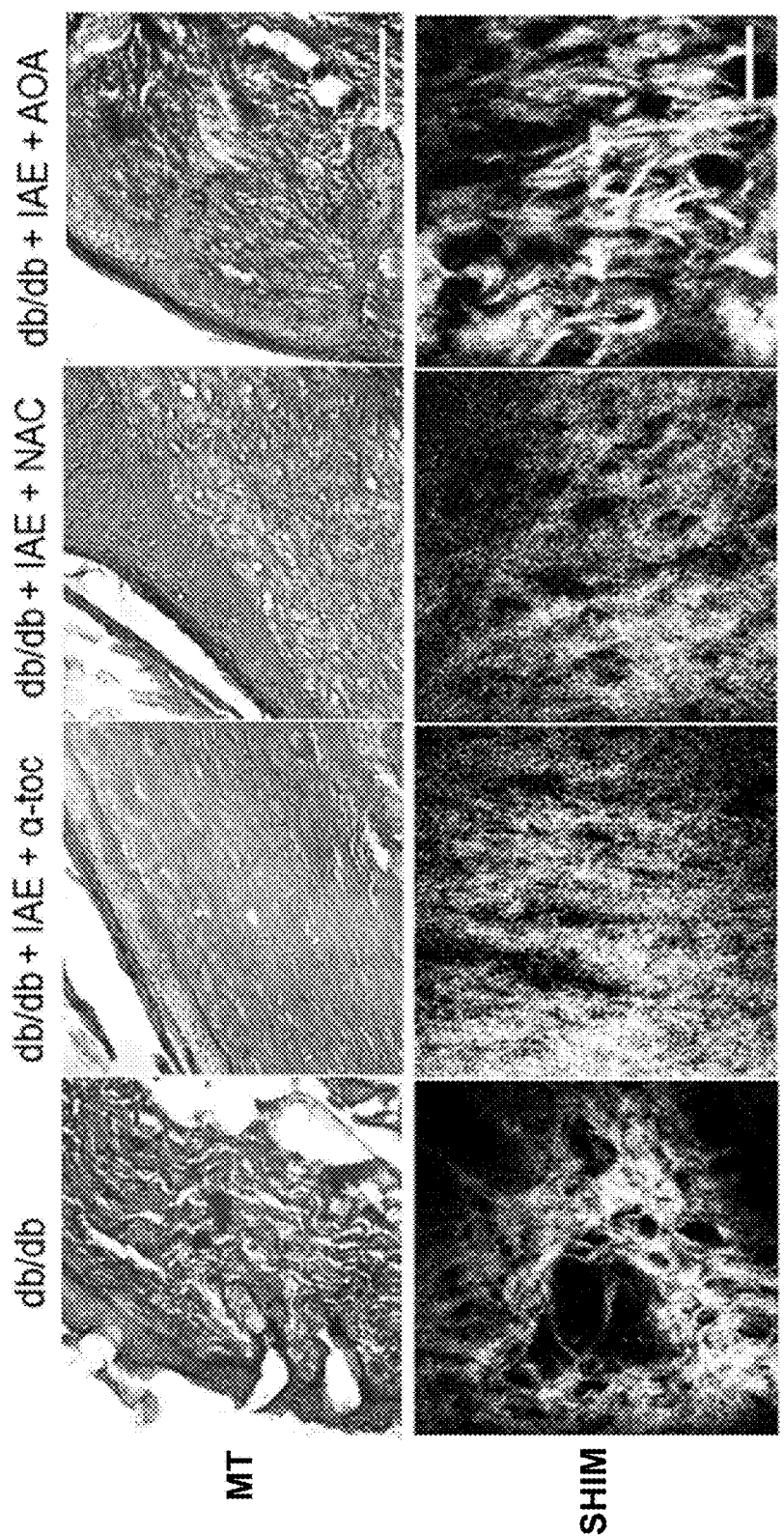
FIG. 20 is a panel indicating that treatment with N-acetyl cysteine and α-tocopherol improves the quality of collagen deposition. The collagen fibers in the granulation tissue are much more mature in the wounds treated with both AOA (NAC and a-Toc).
Figure 21:
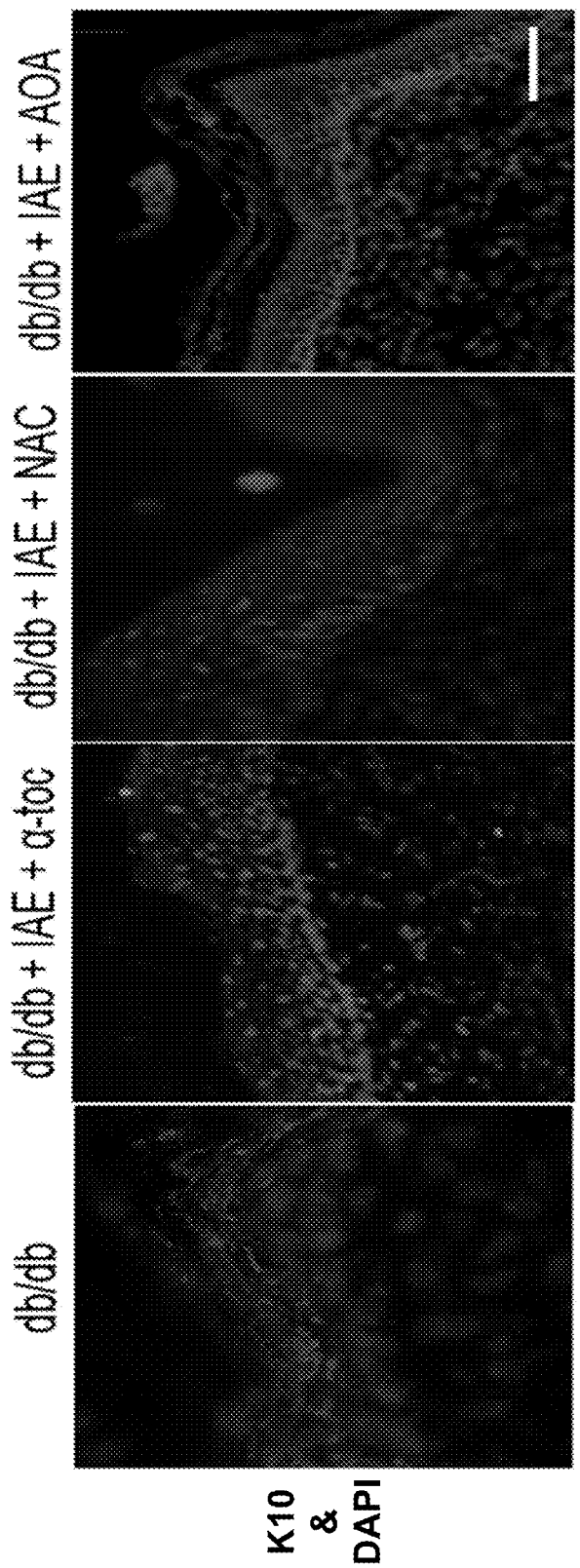
FIG. 21 is a panel indicating that treatment with N-acetyl cysteine and α-tocopherol improves the quality of the epidermis. The epidermis is much more mature in the wounds treated with both AOA (NAC and a-Toc).

To perform the loss of ROS function we treated the wounds with antioxidant agents (AOA). We chose to use N-Acetylcysteine (NAC), an amino acid that is critical for the function of GPx and also breaks down mucus and α-tocopherol (α-Toc) a specific form of Vit E that is a very potent inhibitor of lipid peroxidation. To reverse chronicity, at 20 days when the wounds are considered frankly chronic in this mouse model system, we treated the wounds with NAC topically followed by replacement of the Tegaderm. Simultaneously, the mice were injected intraperitoneally with α-Toc. This treatment continued with NAC applied to the wound topically every day using an insulin syringe to deposit the solution under the Tegarderm and over the wound and with a-Toc IP every-other-day for 20 days (40 days post-wounding). At this point, the antioxidant treatment was stopped and the wounds went on to heal around 30 days after initiation of treatment with antioxidants (50 days post-wounding) (FIG. 12). The oxidative stress was reversed, the biofilm dismantled (FIGS. 13-18) and the quality of the tissue was much improved as detected by histology. We used hematoxylin an eosin staining for general histology (FIG. 19), and Masson-thriochrome and second harmonic generation imaging (SHIM) to examine the quality of the collagen fiber in the granulation (healing) tissue (FIG. 20). We also used immunolabeling to show that the quality of the epidermis was much superior when we used treated with NAC and α-Toc (FIG. 21). For the antioxidant controls, the mice were treated exactly the same way but with vehicle rather than antioxidants.

III. Summary

Inhibition of antioxidant enzymes catalase and GPx in db/db mice upon wounding leads to development of chronic wounds.

Bacteria are observed in db/db mouse chronic wounds as early as 4 days post-wounding, even in the absence of bacterial inoculation.

Impaired healing can be restored by treatment with antioxidants NAC and a-Tocopherol.

Imbalanced levels of oxidative stress markers (SOD, $H_2O_2$, GPx and Catalase), dismantling of the biofilm and improved granulation tissue can be restored with antioxidant treatment.

Dermis and epidermis development during healing is significantly improved by treatment with antioxidants.

Figure 22:
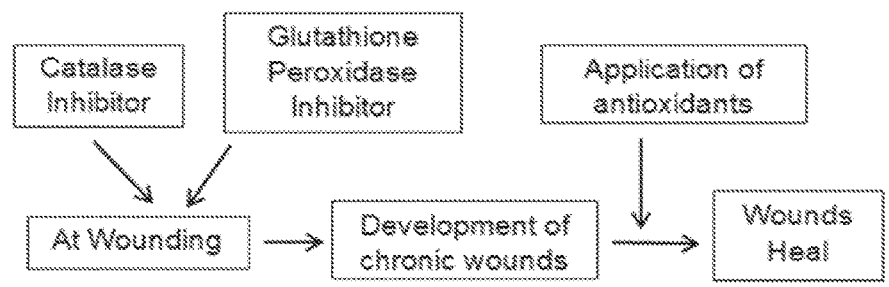
FIG. 22 is a schematic illustration of the framework for experiments. Creating chronic wound is shown on the left side of the schematic, and healing chronic wounds is shown on the right side of the schematic.

The framework for the study is shown in FIG. 22. ps Conclusions

Creation of redox imbalance in the wound microenvironment shortly after wounding in db/db mice leads to the development of chronic wounds with increase in oxidative stress, the presence of biofilm-forming bacteria and high levels of tissue damage.

These effects can be reversed by application of antioxidant agents, leading to reduced oxidative stress, reduced presence of bacteria and improved tissue quality.

Our findings demonstrate the important role of redox balance at the early stages of healing and suggest that treating chronic wounds by debridement followed by treatment of antioxidant agents should lead to significantly improved healing.

We have identified a major underlying trigger mechanism of poor healing that occurs shortly after injury. The implication of these results is that application of antioxidants to chronic wounds after debridement would lead to significantly improved healing.

REFERENCES

The following publications are incorporated by reference herein in their entirety:

1. Maruyama K, Asai J, Ii M, Thorne T, Losordo D W, D'Amore P a: Decreased macrophage number and activation lead to reduced lymphatic vessel formation and contribute to impaired diabetic wound healing. *Am J Pathol* 2007, 170:1178-91.
2. Galiano R D, Tepper O M, Pelo C R, Bhatt K a, Callaghan M, Bastidas N, Bunting S, Steinmetz H G, Gurtner G C: Topical vascular endothelial growth factor accelerates diabetic wound healing through increased angiogenesis and by mobilizing and recruiting bone marrow-derived cells. *Am J Pathol* 2004, 164:1935-47.
3. Lobmann R, Ambrosch a, Schultz G, Waldmann K, Schiweck S, Lehnert H: Expression of matrix-metalloproteinases and their inhibitors in the wounds of diabetic and non-diabetic patients. *Diabetologia* 2002, 45:1011-6.
4. Sen C K, Gordillo G M, Roy S, Kirsner R, Lambert L, Hunt T K, Gottrup F, Gurtner G C, Longaker M T: Human skin wounds: a major and snowballing threat to public health and the economy. *Wound Repair Regen* 2009, 17:763-71.
5. National Diabetes Statistics Report: Estimates of Diabetes and Its Burden in the United States [http://www.cdc.gov/diabetes/pubs/statsreport14.htm]

6. Wlaschek M, Scharffetter-Kochanek K: Oxidative stress in chronic venous leg ulcers. *Wound Repair Regen* 2005, 13:452-61.
7. James T J, Hughes M a, Cherry G W, Taylor R P: Evidence of oxidative stress in chronic venous ulcers. *Wound Repair Regen* 2003, 11:172-6.
8. James G a, Swogger E, Wolcott R, Pulcini E deLancey, Secor P, Sestrich J, Costerton J W, Stewart P S: Biofilms in chronic wounds. *Wound Repair Regen* 2007, 16:37-44.
9. Bjarnsholt T, Kirketerp-Møller K, Jensen P Ø, Madsen K G, Phipps R, Krogfelt K, Høiby N, Givskov M: Why chronic wounds will not heal: a novel hypothesis. *Wound Repair Regen* 2008, 16:2-10.
10. Petreaca M L, Do D, Dhall S, McLelland D, Serafino A, Lyubovitsky J, Schiller N, Martins-Green M M: Deletion of a tumor necrosis superfamily gene in mice leads to impaired healing that mimics chronic wounds in humans. *Wound Repair Regen* 2012, 20:353-66.
11. Greenhalgh D G, Sprugel K H, Murray M J, Ross R: PDGF and FGF stimulate wound healing in the genetically diabetic mouse. *Am J Pathol* 1990, 136:1235-46.
12. Mudge B P, Harris C, Gilmont R R, Adamson B S, Rees R S: Role of glutathione redox dysfunction in diabetic wounds. *Wound Repair Regen* 2002, 10:52-8.
13. Kishimoto T K, Jutila M A, Berg E L, Butcher E C: Neutrophil Mac-1 and MEL-14 adhesion proteins inversely regulated by chemotactic factors. *Science* 1989, 245:1238-41.
14. Ponugoti B, Xu F, Zhang C, Tian C, Pacios S, Graves D T: FOXO1 promotes wound healing through the up-regulation of TGF-β1 and prevention of oxidative stress. *J Cell Biol* 2013, 203:327-43.
15. Sen C K, Roy S: Redox signals in wound healing. *Biochim Biophys Acta* 2008, 1780:1348-61.
16. Gjødsbøl K, Christensen J J, Karlsmark T, Jørgensen B, Klein B M, Krogfelt K A: Multiple bacterial species reside in chronic wounds: a longitudinal study. *Int Wound J* 2006, 3:225-31.
17. Christensen G D, Simpson W a, Younger J J, Baddour L M, Barrett F F, Melton D M, Beachey E H: Adherence of coagulase-negative staphylococci to plastic tissue culture plates: a quantitative model for the adherence of staphylococci to medical devices. *J Clin Microbiol* 1985, 22:996-1006.
18. Kolodkin-Gal I, Cao S, Chai L, Böttcher T, Kolter R, Clardy J, Losick R: A self-produced trigger for biofilm disassembly that targets exopolysaccharide. *Cell* 2012, 149:684-92.
19. Dhall S, Do D, Garcia M, Wijesinghe D S, Brandon A, Kim J, Sanchez A, Lyubovitsky J, Gallagher S, Nothnagel E A, Chalfant C E, Patel R P, Schiller N, Martins-Green M: A novel model of chronic wounds: importance of redox imbalance and biofilm-forming bacteria for establishment of chronicity. *PLoS One* 2014, 9:e109848.
20. Gilbert A: New Colorimetric Methods of Sugar Analysis. *Methods Enzymol* 1962, 184:85-95.
21. Chaplin M F: A rapid and sensitive method for the analysis of carbohydrate components in glycoproteins using gas-liquid chromatography. *Anal Biochem* 1982, 123:336-341.
22. Chambers R E, Clamp J R: An assessment of methanolysis and other factors used in the analysis of carbohydrate-containing materials. *Biochem J* 1971, 125:1009-18.
23. Fu H, Yadav M P, Nothnagel E A: Physcomitrella patens arabinogalactan proteins contain abundant terminal 3-O-methyl-L: -rhamnosyl residues not found in angiosperms. *Planta* 2007, 226:1511-24.
24. Mustoe T a, O'Shaughnessy K, Kloeters O: Chronic wound pathogenesis and current treatment strategies: a unifying hypothesis. *Plast Reconstr Surg* 2006, 117 (7 Suppl):35S-41S.
25. Arnold M, Barbul A: Nutrition and wound healing. *Plast Reconstr Surg* 2006, 117 (7 Suppl):42S-58S.
26. Bonomo S R, Davidson J D, Tyrone J W, Lin X, Mustoe T a: Enhancement of wound healing by hyperbaric oxygen and transforming growth factor beta3 in a new chronic wound model in aged rabbits. *Arch Surg* 2000, 135:1148-53.
27. Feinstein R N, Berliner S, Green F: Mechanism of Inhibition of Catalase By 3-Amino-1,2,4-triazole. *Arch Biochem Biophys* 1957, 76:32-44.
28. Chaudiere J, Wilhelmsen E C, Tappel a L: Mechanism of selenium-glutathione peroxidase and its inhibition by mercaptocarboxylic acids and other mercaptans. *J Blot Chem* 1984, 259:1043-50.
29. Heim W G, Appleman D, Pyfrom H T: Effects of 3-Amino-1,2,4-Triazole (AT) on Catalase and Other Compounds. *Am J Physiol* 1956, 186:19-23.
30. Legg P G, Wood R L: Effects of catalase inhibitors on the ultrastructure and peroxidase activity of proliferating microbodies. *Histochemie* 1970, 22:262-76.
31. Neurobiology B: Pergamon Effects of 3-Amino-1,2,4-Triazole on Brain Catalase in the Mediation of Ethanol Consumption in Mice. 1994, 11:235-239.
32. Guidet B R, Shah S V: In vivo generation of hydrogen peroxide by rat kidney cortex and glomeruli. *Am J Physiol* 1989, 256 (1 Pt 2):F158-64.
33. Kingma J G, Simard D, Rouleau J R, Tanguay R M, Currie R W: Effect of 3-aminotriazole on hyperthermia-mediated cardioprotection in rabbits. *Am J Physiol* 1996, 270 (4 Pt 2):H1165-71.
34. Welker A F, Campos E G, Cardoso L A, Hermes-lima M: Role of catalase on the hypoxia/reoxygenation stress in the hypoxia-tolerant Nile tilapia. 2012.
35. Amantea D, Marrone M C, Nistico R, Federici M, Bagetta G, Bernardi G, Mercuri N B: Oxidative stress in stroke pathophysiology validation of hydrogen peroxide metabolism as a pharmacological target to afford neuroprotection. In *Int Rev Neurobiol. Volume* 85; 2009:363-74.
36. Himes D: Protein-calorie malnutrition and involuntary weight loss: the role of aggressive nutritional intervention in wound healing. *Ostomy Wound Manage* 1999, 45:46-51, 54-5.
37. Siddiqui A R, Bernstein J M: Chronic wound infection: facts and controversies. *Clin Dermatol* 2010, 28:519-26.
38. Percival S L, Hill K E, Malic S, Thomas D W, Williams D W: Antimicrobial tolerance and the significance of persister cells in recalcitrant chronic wound biofilms. *Wound Repair Regen* 2010, 19:1-9.
39. Cho I, Blaser M J: The human microbiome: at the interface of health and disease. *Nat Rev Genet* 2012, 13:260-70.
40. Grice E a, Snitkin E S, Yockey L J, Bermudez D M, Liechty K W, Segre J a: Longitudinal shift in diabetic wound microbiota correlates with prolonged skin defense response. *Proc Natl Acad Sci USA* 2010, 107:14799-804.
41. Khanna S, Biswas S, Shang Y, Collard E, Azad A, Kauh C, Bhasker V, Gordillo G M, Sen C K, Roy S: Macrophage dysfunction impairs resolution of inflammation in the wounds of diabetic mice. *PLoS One* 2010, 5:e9539.

42. Daisuke K, Lee I K, Ishii H, Kanoh H, King G L: Prevention Treatment of Glomerular Dysfunction with d-a-Tocopherol in Diabetic Rats by. *J Am Soc Nephrol* 1997, 8:426-435.
43. Diego-Otero Y de: α-Tocopherol Protects Against Oxidative Stress in the Fragile X Knockout Mouse an Experimental Therapeutic Approach for the Fmr1 Deficiency-.pdf. 2009:1011-1026.
44. Ikeda S, Tohyama T, Yoshimura H, Hamamura K, Abe K, Yamashita K: Dietary alpha-tocopherol decreases alpha-tocotrienol but not gamma-tocotrienol concentration in rats. *J Nutr* 2003, 133:428-34.
45. Senoglu N, Yuzbasioglu M F, Aral M, Ezberci M, Kurutas E B, Bulbuloglu E, Ezberci F, Oksuz H, Ciragil P: Protective effects of N-acetylcysteine and beta-glucan pretreatment on oxidative stress in cecal ligation and puncture model of sepsis. *J Invest Surg* 2008, 21:237-43.
46. Ivanovski O, Szumilak D, Nguyen-Khoa T, Ruellan N, Phan O, Lacour B, Descamps-Latscha B, Drüeke TB, Massy Z a: The antioxidant N-acetylcysteine prevents accelerated atherosclerosis in uremic apolipoprotein E knockout mice. *Kidney Int* 2005, 67:2288-94.
47. Han A, Zenilman J M, Melendez J H, Shirtliff M E, Agostinho A, James G, Stewart P S, Mongodin E F, Rao D, Rickard A H, Lazarus G S: The importance of a multifaceted approach to characterizing the microbial flora of chronic wounds. *Wound Repair Regen* 2011, 19:532-41.
48. James G, Marc A, Hunt A: Imaging Biofilms in Tissue Specimens. In *Antibiofilm Agents*. Volume 8. Edited by Rumbaugh K P, Ahmad I. Berlin, Heidelberg: Springer Berlin Heidelberg; 2014:31-44. [*Springer Series on Biofilms*]
49. Gilmore A. Shirley, Robinson Gretchen, Posthauer Ellen Mary R J: Clinical Indicators Associated with Unintentional Weight loss and Pressure Ulcers in Elderly Residents of Nursing Facilities.pdf. 1995:984-992.
50. Scales B S, Huffnagle G B: The microbiome in wound repair and tissue fibrosis. *J Pathol* 2013, 229:323-31.
51. Grice E A, Segre J A: The skin microbiome. *Nat Rev Microbiol* 2011, 9:244-53.
52. Roth R R, James W D: Microbial ecology of the skin. *Annu Rev Microbiol* 1988, 42:441-64.
53. Hansson C, Hoborn J, Möller A, Swanbeck G: The microbial flora in venous leg ulcers without clinical signs of infection. Repeated culture using a validated standardised microbiological technique. *Acta Derm Venereol* 1995, 75:24-30.
54. Sebeny P J, Riddle M S, Petersen K: Acinetobacter baumannii skin and soft-tissue infection associated with war trauma. *Clin Infect Dis* 2008, 47:444-9.
55. Dowd S E, Sun Y, Secor P R, Rhoads D D, Wolcott B M, James G a, Wolcott R D: Survey of bacterial diversity in chronic wounds using pyrosequencing, DGGE, and full ribosome shotgun sequencing. *BMC Microbiol* 2008, 8:43.
56. Be N a, Allen J E, Brown T S, Gardner S N, McLoughlin K S, Forsberg J a, Kirkup B C, Chromy B a, Luciw P a, Elster E a, Jaing C J: Microbial profiling of combat wound infection through detection microarray and next-generation sequencing. *J Clin Microbiol* 2014 (May).
57. Ma C, Martins-Green M: Second-hand cigarette smoke inhibits wound healing of the cornea by stimulating inflammation that delays corneal reepithelization. *Wound Repair Regen* 2009, 17:387-96.
58. D'Autreaux B, Toledano M B: ROS as signalling molecules: mechanisms that generate specificity in ROS homeostasis. *Nat Rev Mol Cell Biol* 2007, 8:813-24.
59. Roy S, Khanna S, Nallu K, Hunt T K, Sen C K: Dermal wound healing is subject to redox control. *Mol Ther* 2006, 13:211-20.
60. Klyubin I V, Kirpichnikova K M, Gamaley I A: Hydrogen peroxide-induced chemotaxis of mouse peritoneal neutrophils. *Eur J Cell Biol* 1996, 70:347-51.
61. Loo A E K, Wong Y T, Ho R, Wasser M, Du T, Ng W T, Halliwell B: Effects of hydrogen peroxide on wound healing in mice in relation to oxidative damage. *PLoS One* 2012, 7:e49215.
62. Dröge W: Free radicals in the physiological control of cell function. *Physiol Rev* 2002, 82:47-95.
63. Schafer M, Werner S: Oxidative stress in normal and impaired wound repair. *Pharmacol Res* 2008, 58:165-71.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method of treating a mouse to cause it to have a chronic wound whereby the mouse can be used as an animal model, comprising
   creating a fresh wound in a mouse,
   inhibiting at least two antioxidant agents located within the fresh wound, and
   allowing the fresh wound to develop into a chronic wound,
   wherein the inhibiting is performed by administering to the mouse one or more inhibitors of the at least one antioxidant agent, where the one or more inhibitors is an inhibitor of catalase, an inhibitor of glutathione peroxidase, or a combination thereof.

2. A chronic wound animal model prepared by the method of claim 1.

3. A method of screening for an agent that treats chronic wounds, comprising screening a compound for its ability to reduce or heal a chronic wound of an animal model, wherein the animal model results from treating a mouse to cause it to have a chronic wound whereby the mouse can be used as an animal model, comprising:
   creating a fresh wound in a mouse,
   inhibiting at least two antioxidant agents located within the fresh wound, and
   allowing the fresh wound to develop into the chronic wound,
   wherein the inhibiting is performed by administering to the mouse one or more inhibitors of the at least one antioxidant agent, where the one or more inhibitors is an inhibitor of catalase, an inhibitor of glutathione peroxidase, or a combination thereof.

4. The method of claim 3, wherein the mouse is a db/db mouse.

5. The method of claim 3, wherein the at least one antioxidant agent is a free radical scavenger, a lipid peroxidation inhibitor, or a combination thereof.

6. The method of claim 3, wherein the at least one antioxidant agent is catalase, glutathione peroxidase, or a combination thereof.

7. The method of claim 3, wherein the one or more inhibitors is mercaptosuccinic acid, 3-amino-1,2,4-triazole, or a combination thereof.

8. The method of claim 3, wherein the administering is performed before creating the fresh wound or after creating the fresh wound.

9. The method of claim 3, wherein the administering is performed before and after creating the fresh wound.

10. The method of claim 3, wherein the chronic wound comprises a biofilm.

11. The method of claim 3, wherein the allowing comprises covering the fresh wound with a dressing to prevent contamination.

12. The method of claim 1, wherein the one or more inhibitors is mercaptosuccinic acid, 3-amino-1,2,4-triazole, or a combination thereof.

* * * * *